(12) United States Patent
Mehrling

(10) Patent No.: US 11,576,899 B2
(45) Date of Patent: Feb. 14, 2023

(54) TINOSTAMUSTINE FOR USE IN TREATING SARCOMA

(71) Applicant: Purdue Pharma L.P., Stamford, CT (US)

(72) Inventor: Thomas Jorg Mehrling, Basel (CH)

(73) Assignee: Purdue Pharma L.P., Stamford, CT (US)

( * ) Notice: Subject to any disclaimer, the term of this patent is extended or adjusted under 35 U.S.C. 154(b) by 463 days.

(21) Appl. No.: 16/621,885

(22) PCT Filed: Jun. 13, 2018

(86) PCT No.: PCT/EP2018/065668
§ 371 (c)(1),
(2) Date: Dec. 12, 2019

(87) PCT Pub. No.: WO2018/229133
PCT Pub. Date: Dec. 20, 2018

(65) Prior Publication Data
US 2020/0113870 A1    Apr. 16, 2020

(30) Foreign Application Priority Data
Jun. 13, 2017 (GB) .................. 1709403

(51) Int. Cl.
*A61K 31/4184* (2006.01)
*A61P 35/00* (2006.01)
*A61N 5/10* (2006.01)

(52) U.S. Cl.
CPC ........... *A61K 31/4184* (2013.01); *A61N 5/10* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,461,350 B2 | 6/2013 | Brittain et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 9,889,147 B2 | 2/2018 | Utku |
| 9,993,482 B2 | 6/2018 | Mehrling |
| 10,118,901 B2 | 11/2018 | Chen et al. |
| 10,406,138 B2 | 9/2019 | Mehrling et al. |
| 10,744,120 B2 | 8/2020 | Mehrling et al. |
| 11,266,631 B2 | 3/2022 | Mehrling et al. |
| 11,318,117 B2 | 5/2022 | Mehrling et al. |
| 11,413,276 B2 | 8/2022 | Mehrling |
| 11,419,853 B2 | 8/2022 | Mehrling et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2012/0289570 A1 | 11/2012 | Lengyel et al. |
| 2013/0030237 A1 | 1/2013 | Theuer |
| 2013/0209558 A1 | 8/2013 | Patzak et al. |
| 2015/0086551 A1 | 3/2015 | Chen et al. |
| 2015/0231198 A1 | 8/2015 | Carniti et al. |
| 2017/0095482 A1 | 4/2017 | Mehrling |
| 2017/0151218 A1 | 6/2017 | Mehrling et al. |
| 2018/0098969 A1 | 4/2018 | Mehrling et al. |
| 2019/0343807 A1 | 11/2019 | Mehrling et al. |
| 2020/0113870 A1 | 4/2020 | Mehrling |
| 2020/0261423 A1 | 8/2020 | Mehrling |
| 2021/0059989 A1 | 3/2021 | Mehrling et al. |
| 2021/0346351 A1 | 11/2021 | Mehrling et al. |
| 2022/0016084 A1 | 1/2022 | Hilgier et al. |
| 2022/0016085 A1 | 1/2022 | Hilgier et al. |

FOREIGN PATENT DOCUMENTS

| | | |
|---|---|---|
| CL | 0501-2003 | 3/2003 |
| CL | 2272-2005 | 9/2005 |
| CL | 3232-2006 | 11/2006 |

(Continued)

OTHER PUBLICATIONS

Victoria White, European Pharmaceutical Review Magazine, Aug. 3 (Year: 2015).*
Advanced Accelerator Applications, Ongoing Clinical Studies with Advanced Accelerator Applications Pipeline Candidates. Retrieved online at: http://www.adacap.com/research-development/clinical-trials/. 6 pages, (2014).
Aguado Bueno et al., Preliminary Experience of the Spanish Compassionate Use Registry of Bendamustine in Patients with Relapsed and/or Refractory Multiple Myeloma. Blood. 2012;120(21), Abstract 4035.
Al-Ani et al., Changes in urinary metabolomic profile during relapsing renal vasculitis. Sci Rep. Dec. 1, 2016;6:38074. 11 pages.

(Continued)

*Primary Examiner* — Zinna Northington Davis

(74) *Attorney, Agent, or Firm* — McCarter & English, LLP; Yu Lu

(57) ABSTRACT

There is provided tinostamustine or a pharmaceutically acceptable salt thereof for use in the treatment of sarcoma in a patient in need thereof.

20 Claims, 2 Drawing Sheets

(56) References Cited

FOREIGN PATENT DOCUMENTS

| | | | |
|---|---|---|---|
| CN | 1764648 A | 4/2006 |
| CN | 101084876 A | 12/2007 |
| CN | 101928234 A | 12/2010 |
| CN | 102993102 A | 3/2013 |
| DE | 34727 A1 | 12/1964 |
| EP | 0717638 B1 | 3/2002 |
| EP | 3148529 A1 | 4/2017 |
| JP | 2007-531793 A | 11/2007 |
| WO | WO-1995/030442 A1 | 11/1995 |
| WO | WO-2002/010161 A1 | 2/2002 |
| WO | WO-2002/22577 A2 | 3/2002 |
| WO | WO-2002/026696 A1 | 4/2002 |
| WO | WO-2002/055017 A2 | 7/2002 |
| WO | WO-2004/076386 A2 | 9/2004 |
| WO | WO-2005/013958 A1 | 2/2005 |
| WO | WO-2005/097747 A1 | 10/2005 |
| WO | WO-2006/120456 A1 | 11/2006 |
| WO | WO-2007/134169 A2 | 11/2007 |
| WO | WO-2008/050125 A1 | 5/2008 |
| WO | WO-2008/067027 A2 | 6/2008 |
| WO | WO-2009/036016 A1 | 3/2009 |
| WO | WO-2009/067453 A1 | 5/2009 |
| WO | WO-2009/100045 A1 | 8/2009 |
| WO | WO-2010/042568 A1 | 4/2010 |
| WO | WO-2010/075542 A1 | 7/2010 |
| WO | WO 2010/085377 A2 * | 7/2010 |
| WO | WO-2010/097700 A1 | 9/2010 |
| WO | WO-2011/017448 A1 | 2/2011 |
| WO | WO-2013/039488 A1 | 3/2013 |
| WO | WO 2013/040286 A2 * | 3/2013 |
| WO | WO-2013/113838 A1 | 8/2013 |
| WO | WO-2015/085289 A1 | 6/2015 |
| WO | WO-2015/180865 A1 | 12/2015 |
| WO | WO-2015/181154 A1 | 12/2015 |
| WO | WO-2015/181156 A1 | 12/2015 |
| WO | WO-2015/181157 A1 | 12/2015 |
| WO | WO-2016/087950 A1 | 6/2016 |
| WO | WO-2017/067474 A1 | 4/2017 |

OTHER PUBLICATIONS

Alfarouk et al., Resistance to cancer chemotherapy: failure in drug response from ADME to P-gp. Cancer Cell Int. Jul. 15, 2015;15:71.
American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).
Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.
Andersson et al., Discovery of novel drug sensitivities in T-PLL by high-throughput ex vivo drug testing and mutation profiling. Leukemia. Aug. 14, 2017. Pages 1-14.
Andersson et al., Primary T-Prolymphocytic Leukemia (T-PLL) Cells Are Sensitive To BCL-2 and HDAC Inhibitors: Results From High-Throughput Ex Vivo Drug Testing. Blood. 2013;122:3828. 6 pages.
Angelucci et al., Suberoylanilide hydroxamic acid partly reverses resistance to paclitaxel in human ovarian cancer cell lines. Gynecol Oncol. Dec. 2010;119(3):557-63.
Arun et al., The PARP inhibitor AZD2281 (Olaparib) induces autophagy/mitophagy in BRCA1 and BRCA2 mutant breast cancer cells. Int J Oncol. Jul. 2015;47(1):262-8.
Attal et al., Lenalidomide, Bortezomib, and Dexamethasone with Transplantation for Myeloma. The New England Journal of Medicine. Apr. 6, 2017;376:1311-1320.
Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.
Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22.
Bagchi, Bendamustine for advanced sarcoma. Lancet Oncol. Aug. 2007;8(8):674.
Baker et al., Investigation of bendamustine HCL in a phase 2 study in women with resistant ovarian cancer. Invest New Drugs. Feb. 2013;31(1):160-6.
Balfour et al., Bendamustine. Drugs. 2001;61(5):631-8.
Barendsen et al., Inhibition of TPA-induced monocytic differentiation in THP-1 human monocytic leukemic cells by staurosporine, a potent protein kinase C inhibitor. Leuk Res. 1990;14(5):467-74.
Bender, Across the divide. The blood-brain barrier represents a formidable obstacle for cancer drugs. Nature. Sep. 27, 2018;561:S46-S47.
Berenson et al., Phase I/II trial assessing bendamustine plus bortezomib combination therapy for the treatment of patients with relapsed or refractory multiple myeloma. Br J. Haematol. Feb. 2013;160(3):321-30.
Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.
Besse et al., The first in class, alkylator-histone-deacetylase-inhibitor fusion molecule EDO-S101 in combination with proteasome inhibitors induces highly synergistic pro-apoptotic signaling through UPR activation and suppression of c-Myc and BCL2 in multiple meyloma. ASH, 2016.
Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.
Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.
Biete et al., Whole abdominal radiotherapy in ovarian cancer. Rep Pract Oncol Radiother. Mar. 23, 2010;15(2):27-30.
Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.
Bose et al., Histone deacetylase inhibitor (HDACI) mechanisms of action: emerging insights. Pharmacol Ther. Sep. 2014;143(3):323-36.
Botrugno et al., Molecular pathways: old drugs define new pathways: non-histone acetylation at the crossroads of the DNA damage response and autophagy. Clin Cancer Res. May 1, 2012;18(9):2436-42.
Braga et al., Crystal Polymorphism and Multiple Crystal Forms. Struct Bond. 2009;132:25-50.
Brewster et al., Cyclodextrins as pharmaceutical solubilizers. Adv Drug Deliv Rev. Jul. 30, 2007;59(7):645-66.
Bruce et al., Glioblastoma Multiforme Treatment & Management. Medscape. Retrieved online at: https://emedicine.medscape.com/article/283252-treatment. 20 pages. Jun. 14, 2017.
Buglio et al., Histone deacetylase inhibitors in Hodgkin lymphoma. Invest New Drugs. Dec. 2010;28 Suppl 1:S21-7.
Buglio et al., Vorinostat inhibits STAT6-mediated TH2 cytokine and TARC production and induces cell death in Hodgkin lymphoma cell lines. Blood. Aug. 18, 2008;112(4):1424-33.
Cai et al., Combination of bendamustine and entinostat synergistically inhibits proliferation of multiple myeloma cells via induction of apoptosis and DNA damage response. Cancer Lett. Jul. 28, 2013;335(2):343-50.
Cai et al., Discovery of 7-(4-(3-ethynylphenylamino)-7-methoxyquinazolin-6-yloxy)-N-hydroxyheptanamide (CUDc-101) as a potent multi-acting HDAC, EGFR, and HER2 inhibitor for the treatment of cancer. J Med Chem. Mar. 11, 2010;53(5):2000-9.
Cai et al., Solubilization of vorinostat by cyclodextrins. J Clin Pharm Ther. Oct. 2010;35(5):521-6.

(56) References Cited

OTHER PUBLICATIONS

Campos et al., Expression of nuclear receptor corepressors and class I histone deacetylases in astrocytic gliomas. Cancer Sci. Feb. 2011;102(2):387-92.

Chamberlain et al., Salvage therapy with bendamustine for methotrexate refractory recurrent primary CNS lymphoma: a retrospective case series. J Neurooncol. May 2014;118(1):155-62.

Chamberlain et al., Salvage therapy with single agent bendamustine for recurrent glioblastoma. J Neurooncol. Dec. 2011;105(3):523-30.

Chavez et al., Triple negative breast cancer cell lines: one tool in the search for better treatment of triple negative breast cancer. Breast Dis. 2010;32(1-2):35-48.

Chen et al., A 71-gene signature of TRAIL sensitivity in cancer cells. Mol Cancer Ther. Jan. 2012;11(1):34-44.

Chen et al., Dexamethasone and vorinostat cooperatively promote differentiation and apoptosis in Kasumi-1 leukemia cells through ubiquitination and degradation of AML1-ETO. Zhonghua Xue Ye Xue Za Zhi. Sep. 2013;34(9):741-4.

Chen et al., Discovery of a Novel, Efficient, and Scalable Route to Bendamustine Hydrochloride: The API in Treanda. Org Process Res Dev. 2011;15(5):1063-1072.

Chesi et al., Drug response in a genetically engineered mouse model of multiple myeloma is predictive of clinical efficacy. Blood. Jul. 12, 2012;120(2):376-85.

Chesi et al., Identification of Novel Therapeutic Targets in the Clinically Predictive Vk*MYC Mouse Model of Multple Myeloma. ASH, 2 pages. 2014.

Chesi et al., Identification of Novel Therapeutic Targets in the Clinically Predictive Vk*MYC Mouse Model of Multple Myeloma. Blood. 2014;124:415.

Chisholm et al., Emergence of drug tolerance in cancer cell populations: an evolutionary outcome of selection, nongenetic instability, and stress-induced adaptation. Cancer Res. Mar. 15, 2015;75(6):930-9.

Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.

Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.

Chow et al., In vitro induction of apoptosis of neoplastic cells in low-grade non-Hodgkin's lymphomas using combinations of established cytotoxic drugs with bendamustine. Haematologica. May 2001;86(5):485-93.

Ciavatta et al., Epigenetic basis for aberrant upregulation of autoantigen genes in humans with ANCA vasculitis. J Clin Invest. Sep. 2010;120(9):3209-19.

Ciusani et al., Valproic acid increases the in vitro effects of nitrosureas on human glioma cell lines. Oncol Res. 2007;16(10):453-63.

Clinicaltrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.

Clinicaltrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.

Clinicaltrials.gov, Phase 1 Trial of Dasatinib and Bendamustine in Chronic Lymphocytic Leukemia. ClinicalTrials Identifier: NCT00872976, Apr. 22, 2009. 3 pages.

Clinicaltrials.gov, Study of EDO-S101, A First-in-Class Alkylating HDACi Fusion Molecule, in Relapsed/Refractory Hematologic Malignancies. ClinicalTrials.gov Identifier: NTC02576496, 4 pages, Oct. 2015.

Clinicaltrials.gov, Study of the Safety, Pharmacokinetics and Efficacy of EDO-S101, in Patients With Advanced Solid TumorsClinical Trials Identifier: NCT03345485, Dec. 24, 2020. 12 pages.

Connors, Hodgkin lymphoma: special challenges and solutions. Hematol Oncol. Jun. 2015;33 Suppl 1:21-4.

Cooke et al., Spontaneous onset and transplant models of the Vk*MYC mouse show immunological sequelae comparable to human multiple myeloma. J Transl Med. Sep. 6, 2016;14:259. 12 pages.

Corazzelli et al., Efficacy and safety of bendamustine for the treatment of patients with recurring Hodgkin lymphoma. Br J Haematol. Jan. 2013;160(2):207-15.

Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Blood. 2015;126(23):2479. 7 pages.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1 page.

De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [htps://ash.confex.com/ash/2015/webprogram/Paper84797.html]. 2 pages.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. Blood. 2015;126:2481, 5 pages.

Deangelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.

Desouza et al., Has the survival of patients with glioblastoma changed over the years? Br J Cancer. Jan. 19, 2016;114(2):146-50.

Detich et al., Valproate induces replication-independent active DNA demethylation. J Biol Chem. Jul. 25, 2003;278(30):27586-92.

Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.

Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.

Drogaris et al., Histone deacetylase inhibitors globally enhance h3/h4 tail acetylation without affecting h3 lysine 56 acetylation. Sci Rep. 2012;2:220. 12 pages.

Döhner et al., Diagnosis and management of acute myeloid leukemia in adults: recommendations from an international expert panel, on behalf of the European LeukemiaNet. Blood. Jan. 21, 2010;115(3):453-74.

Edoncology.Com, The A-DAC Principle: A New Concept in Oncology Treatment. 3 pages, Sep. 2016.

EU Clinical Trials Register, EudraCT No. 2005-002051-41. 13 pages. Dec. 7, 2016.

EU Clinical Trials Register, EudraCT No. 2005-006083-57. 28 pages. Jun. 1, 2016.

Eurordis, Rare Diseases Europe, Why Research on Rare Diseases? Position Paper. Retrieved online at: www.eurordis.org. 14 pages. Oct. 2010.

(56) References Cited

OTHER PUBLICATIONS

Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.

Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.

Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.

Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.

Formenti et al., Results of a phase I-II study of adjuvant concurrent carboplatin and accelerated radiotherapy for triple negative breast cancer. Oncoimmunology. Dec. 27, 2016;6(3):e1274479, 8 pages.

Frew et al., Enhancing the apoptotic and therapeutic effects of HDAC inhibitors. Cancer Lett. Aug. 8, 2009;280(2):125-33.

Furumai et al., Potent histone deacetylase inhibitors built from trichostatin A and cyclic tetrapeptide antibiotics including trapoxin. Proc Natl Acad Sci USA. Jan. 2, 2001;98(1):87-92.

Geurink et al., Incorporation of non-natural amino acids improves cell permeability and potency of specific inhibitors of proteasome trypsin-like sites. J Med Chem. Feb. 14, 2013;56(3):1262-75.

Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.

Gillis, HDAC Inhibition Appears to Sensitive Triple-Negative Breast Cancer Cells to Certain Treatments. Retrieved online at: https://www.onclive.com/conference-coverage/sabcs-2012/hdac-inhibition-appears-to-sensitize-triplenegative-breast-cancer-cells-to-certain-treatment, 2 pages, (2012).

Golub et al., Molecular classification of cancer: class discovery and class prediction by gene expression monitoring. Science. Oct. 15, 1999;286(5439):531-7.

Graham et al., T-cell prolymphocytic leukemia. Proc (Bayl Univ Med Cent). Jan. 2013;26(1):19-21.

Gravina et al., The novel CXCR4 antagonist, PRX177561, reduces tumor cell proliferation and accelerates cancer stem cell differentiation in glioblastoma preclinical models. Tumor Biology. Jun. 2017;1-17.

Greaves et al., Clonal evolution in cancer. Nature. Jan. 18, 2012;481(7381):306-13.

Griffith et al., A novel anti-cancer bifunctional platinum drug candidate with dual DNA binding and histone deacetylase inhibitory activity. Chem Commu (Camb). Nov. 28, 2009;(44):6735-7.

Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.

Groselj et al., Histone deacetylase inhibitors as radiosensitisers: effects on DNA damage signalling and repair. Br J Cancer. Mar. 5, 2013;108(4):748-54.

Guntner et al., Cerebrospinal fluid penetration of targeted therapeutics in pediatric brain tumor patients. Acta Neuropathol Commun. Jun. 3, 2020;8(1):78, 13 pages.

Hancock et al., HDAC inhibitor therapy in autoimmunity and transplantation. Ann Rheum Dis. Apr. 2012;71 Suppl 2:i46-54.

Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.

Hartmann et al., Bendamustine hydrochloride in patients with refractory soft tissue sarcoma: a noncomparative multicenter phase 2 study of the German sarcoma group (AIO-001). Cancer. Aug. 15, 2007;110(4):861-6.

Hedgethorne et al., FORETINIB, c-Met and VEGFR-2 Inhibitor Oncolytic. Drugs of the Future. 2010;35(11):893-902.

Hegi et al., MGMT gene silencing and benefit from temozolomide in glioblastoma. N Engl J Med. Mar. 10, 2005;352(10):997-1003.

Her et al., Targeting DNA Double-strand Break Repair in Cancer Therapy. Journal of Molecular and Genetic Medicine. Dec. 31, 2015;9:e106, 1 page.

Herbaux et al., Bendamustine is effective in T-cell prolymphocytic leukaemia. Br J Haematol. Mar. 2015;168(6):916-9.

Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO#19). J Cancer Res Clin Oncol. Feb. 2006;132(2):105-12.

Herold et al., BOP versus COP in Advanced Low Grade Non-Hodgkin's Lymphomas—Results of a Randomized Multicenter Study. Blood. 1999;94:262b. Abstract 4382.

Hideshima et al., Mechanism of action of proteasome inhibitors and deacetylase inhibitors and the biological basis of synergy in multiple myeloma. Mol Cancer Ther. Nov. 2011;10(11):2034-42.

Hoffman, Brentuximab Vedotin Plus Bendamustine Active In Heavily Pretreated Hodgkin Lymphoma, ALCL. Cancer Therapy Advisor, Dec. 7, 2015. 2 pages, retreived online at: http://www.cancertherapyadvisor.com/ash-2015/hodgkin-lymphoma-alcl-brentuximab-vedotin-better-treatment-risk/article/458249/.

Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.

Howlader et al., Contributions of Subtypes of Non-Hodgkin Lymphoma to Mortality Trends. Cancer Epidemiol Biomarkers Prev. Jan. 2016;25(1):174-9.

Hummel et al., A pediatric phase 1 trial of vorinostat and temozolomide in relapsed or refractory primary brain or spinal cord tumors: a Children's Oncology Group phase 1 consortium study. Pediatr Blood Cancer. Sep. 2013;60(9):1452-7.

Ihle et al., HR23b expression is a potential predictive biomarker for HDAC inhibitor treatment in mesenchymal tumours and is associated with response to vorinostat. The Journal of Pathology: Clinical Research. 2016;2:59-71.

Jagannath et al., Bortezomib in combination with dexamethasone for the treatment of patients with relapsed and/or refractory multiple myeloma with less than optimal response to bortezomib alone. Haematologica. Jul. 2006;91(7):929-34.

Jawhari et al., In Vitro and In Vivo Preclinical Activity of EDO-S101 in Hodgkin Lymphoma. Haematologica. 2016;101(s5):6-7, Abstract P037.

Jennette et al., Pathogenesis of antineutrophil cytoplasmic autoantibody-mediated disease Nat Rev Rheumatol. Aug. 2014;10(8):463-73.

Jiang et al., A mammalian functional-genetic approach to characterizing cancer therapeutics. Nature Chemical Biology. Feb. 2011;7:92-100.

Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.

Kalin et al., Creating zinc monkey wrenches in the treatment of epigenetic disorders. Curr Opin Chem Biol. Jun. 2009;13(3):263-71.

Kallenberg, Pathogenesis and treatment of ANCA-associated vasculitides. Clin Exp Rheumatol. Jul.-Aug. 2015;33(4 Suppl 92):S11-4.

Kallenberg, Pathogenesis of ANCA-associated vasculitides. Ann Rheum Dis. Mar. 2011;70 Suppl 1 :i59-63.

Kalsi et al., The impact of low-grade toxicity in older people with cancer undergoing chemotherapy. Br J Cancer. Dec. 9, 2014;111(12):2224-8.

Kampa-Schittenhelm et al., Quizartinib (AC220) is a potent second generation class III tyrosine kinase inhibitor that displays a distinct

(56) References Cited

OTHER PUBLICATIONS inhibition profile against mutant-FLT3, -PDGFRA and -KIT isoforms. Molecular Cancer. 2013;12:19, 15 pages.

Kaufman et al., Lenalidomide. Bortezomib. and Dexamethasone (RVD) in Combination with Vorinostat as Front-Line Therapy for Patients with Multiple Myeloma (MM): Results of a Phase 1 Study. Blood. 2012;120, Abstract No. 336. 2 pages. ASH Annual Meeting.

Keating et al., Bendamustine. Nat Rev Drug Discov. Jun. 2008;7(6):473-4.

Khot et al., Panobinostat in lymphoid and myeloid malignancies. Expert Opin Investig Drugs. Sep. 2013;22(9):1211-23.

Kigawa, New strategy for overcoming resistance to chemotherapy of ovarian cancer. Yonago Acta Med. Jun. 2013;56(2):43-50.

Kim et al., Histone deacetylase inhibitors: molecular mechanisms of action and clinical trials as anti-cancer drugs. Am J Transl Res. Feb. 2011;3(2):166-79.

Knauf, Bendamustine in the treatment of chronic lymphocytic leukemia. Expert Rev Anticancer Ther. Feb. 2009;9(2):165-74.

Knittel et al., Two mouse models reveal an actionable PARP1 dependence in aggressive chronic lymphocytic leukemia. Nat Commun. Jul. 28, 2017;8(1):153. 13 pages.

Kollmannsberger et al., Phase II study of bendamustine in patients with relapsed or cisplatin-refractory germ cell cancer. Anticancer Drugs. Aug. 2000;11(7):535-9.

Koster et al., Carboplatin in Combination with Bendamustine in Previously Untreated Patients with Extensive-Stage Small Cell Lung Cancer (SCLC). Clin Drug Investig. 2004;24(10):611-8.

Kotzin et al., Reversal of nzb/nzw disease with total lymphoid irradiation. J Exp Med. Aug. 1, 1979;150(2):371-8.

Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.

Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.

Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.

Krause et al., Tyrosine kinases as targets for cancer therapy. N Engl J Med. Jul. 14, 2005;353(2):172-87.

Kumar et al., Histone deacetylase inhibitors induce cell death in supratentorial primitive neuroectodermal tumor cells. Oncol Rep. Nov. 2006;16(5):1047-52.

Lala et al., Role of nitric oxide in tumor progression: lessons from experimental tumors. Cancer Metastasis Rev. Mar. 1998;17(1):91-106.

Layman et al., Severe and prolonged lymphopenia observed in patients treated with bendamustine and erlotinib for metastatic triple negative breast cancer. Cancer Chemother Pharmacol. May 2013;71(5):1183-90.

Le Moigne et al., the p97 Inhibitor CB-5083 Is a Unique Disrupter of Protein Homeostasis in Models of Multiple Myeloma. Molecular Cancer Therapeutics. Nov. 2017;16(11):2375-2386.

Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.

Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.

Lentzsch et al., Combination of bendamustine, lenalidomide, and dexamethasone (BLD) in patients with relapsed or refractory multiple myeloma is feasible and highly effective: results of phase 1/2 open-label, dose escalation study. Blood. May 17, 2012;119(20):4608-13.

Leoni et al., Bendamustine (Treanda) displays a distinct pattern of cytotoxicity and unique mechanistic features compared with other alkylating agents. Clin Cancer Res. Jan. 1, 2008;14(1):309-17.

Leoni, Bendamustine: rescue of an effective antineoplastic agent from the mid-twentieth century. Semin Hematol. Apr. 2011;48 Suppl 1:S4-11.

Leung-Hagesteijn et al., Xbp1s-negative tumor B cells and pre-plasmablasts mediate therapeutic proteasome inhibitor resistance in multiple myeloma. Cancer Cell. Sep. 9, 2013;24(3):289-304.

Li et al., Pharmacokinetics of bendamustine in the central nervous system: chemoinformatic screening followed by validation in a murine model. MedChemComm. 2012;3:1526-1530.

Liby et al., Elevated and Deregulated Expression of HDAC3 in Human Astrocytic Glial Tumours. Folia Biologica (Praha). 2006;52:21-33.

Lin et al., Anti-rheumatic activities of histone deacetylase (HDAC) inhibitors in vivo in collagen-induced arthritis in rodents. Br J Pharmacol. Apr. 2007;150(7):862-72.

Lin et al., Treatment of Brain Metastases. J Clin Oncol. Oct. 20, 2015;33(30):3475-84.

Little et al., Experimental autoimmune vasculitis: an animal model of anti-neutrophil cytoplasmic autoantibody-associated systemic vasculitis. Am J Pathol. Apr. 2009;174(4):1212-20.

Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.

Liu et al., A DNA/HDAC dual-targeting drug CY190602 with significantly enhanced anticancer potency. EMBO Mol Med. 12 pages, Published online: Mar. 9, 2015.

Liu et al., Effects of suberoylanilide hydroxamic acid (SAHA) combined with paclitaxel (PTX) on paclitaxel-resistant ovarian cancer cells and insights into the underlying mechanisms. Cancer Cell Int. Nov. 26, 2014;14(1):112, 11 pages.

Liu, Characterization of TCL1-Tg:P53- / -Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.

Loftsson et al., Historical Perspectives: Cyclodextrins and their pharmaceutical applications. International Journal of Pharmaceutics. 2007;329:1-11.

Loibl et al., Multicenter Phase II Study with Weekly Bendamustine and Paclitaxel as First- or Later-Line Therapy in Patients with Metastatic Breast Cancer: RiTa II Trial. Breast Care (Basel). Dec. 2011;6(6):457-461.

Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.

Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.

Lopez-Iglesias et al., Preclinical anti-myeloma activity of the alkylating-HDACi Fusion Molecule EDO-S101 Through DNA-damaging and HDACi Effects. Haematologica. 2014;99(s1):354-355, Abstract P942.

Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.

Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.

Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26m 2015. Rome, Italy. Clinical Lymphoma, Myeloma & Leukemia. Sep. 2015;15(3 Suppl. 3):e218, Abstract P0-238.

Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

(56) References Cited

OTHER PUBLICATIONS

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.
Ludwig et al., Bendamustine-bortezomib-dexamethasone is an active and well-tolerated regimen in patients with relapsed or refractory multiple myeloma. Blood. Feb. 13, 2014;123(7):985-91.
Marchion et al., Development of histone deacetylase inhibitors for cancer treatment. Expert Rev Anticancer Ther. Apr. 2007;7(4):583-98.
Marks, Discovery and development of SAHA as an anticancer agent. Oncogene. Feb. 26, 2007;26(9):1351-6.
Marmion et al., Hydroxamic Acids—An Intriguing Family of Enzyme Inhibitors and Biomedical Ligands. Eur J Inorg Chem. 2004(15):3003-3016.
McInnis et al., Dysregulation of autoantigen genes in ANCA-associated vasculitis involves alternative transcripts and new protein synthesis. J Am Soc Nephrol. Feb. 2015;26(2):390-9.
Meanwell, Synopsis of some recent tactical application of bioisosteres in drug design. J Med Chem. Apr. 28, 2011;54(8):2529-91.
Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.
Mehrling et al., Is there hope to treat glioblastoma effectively? CNS Oncol. 2015;4(6):377-9.
Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.
Mehrling, Chemotherapy is getting 'smarter'. Future Oncol. 2015;11(4):549-52.
Mehrling, First in human clinical trails to commence Q3 2015. Mundipharma EDO GmbH. Retrieved online at: http://mundipharma-edo.com. Jul. 31, 2015. 2 pages.
Mehrling, First-in-human clinical trial of its lead compound, EDO-S101. Mundipharma EDO GmbH. Retrieved online at: http://mundipharma-edo.com. May 31, 2016. 2 pages.
Mehrling, Fusion Therapy, a New Approach to Combining Treatments. Drug Discovery World. 2016;71-76.
Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-cancer-compound-edo-s101-for-the-treatment-of-patients-with-relapsedrefractory-haematologic-malignancies-and-s/. 2 pages, Jul. 31, 2015.
Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.
Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.
Miller et al., Histone deacetylase inhibitors. J Med Chem. Nov. 20, 2003;46(24):5097-116.
Min et al., Histone deacetylase inhibitor, suberoylanilide hydroxamic acid (SAHA), enhances anti-tumor effects of the poly (ADP-ribose) polymerase (PARP) inhibitor olaparib in triple-negative breast cancer cells. Breast Cancer Res. Mar. 7, 2015;17:33, 13 pages.
Minucci et al., Histone deacetylase inhibitors and the promise of epigenetic (and more) treatments for cancer. Nat Rev Cancer. Jan. 2006;6(1):38-51.
Mishra et al., Histone deacetylase inhibitors modulate renal disease in the MRL-Ipr/Ipr mouse. J Clin Invest. Feb. 2003;111(4):539-52.
Moosman et al., Weekly treatment with a combination of bortezomib and bendamustine in relapsed or refractory indolent non-Hodgkin lymphoma. Leuk Lymphoma. Jan. 2010;51(1):149-52.
Moradei et al., Histone deacetylase inhibitors: latest developments, trends and prospects. Curr Med Chem Anticancer Agents. Sep. 2005;5(5):529-60.
Moreau et al., Phase 1b Dose Escalation Study of Oral Quisinostat, a Histone Deacetylase Inhibitor (HDACi), in Combination With Velcade (Bortezomib) and Dexamethasone for Patients With Relapsed Multiple Myeloma (MM). Blood. Nov. 15, 2013;122(21):1932.
Moreau et al., Proteasome inhibitors in multiple myeloma: 10 years later. Blood. Aug. 2, 2012;120(5):947-59.
Moscovitch et al., Successful treatment of autoimmune manifestations in MRL/I and MRL/n mice using total lymphoid irradiation (TLI). Exp Mol Pathol. Feb. 1983;38(1):33-47.
Moskowitz et al., Phase II study of bendamustine in relapsed and refractory Hodgkin lymphoma. J Clin Oncol. Feb. 1, 2013;31(4):456-60.
Moskowitz, Bendamustine: a bridge to longer term solutions in heavily treated Hodgkin lymphoma. Leuk Lymphoma. Nov. 2013;54(11):2339-40.
Mrf, Melanoma Research Foundation, Melanoma Central Nervous System Metastases, Current Approaches, Challenges and Opportunities. 5 pages (2015).
Munakata et al., The discovery and the development of bendamustine for the treatment of non-Hodgkin lymphoma. Expert Opin Drug Discov. Nov. 2016;11(11):1123-1130.
Munker et al., Activity of Tyrosine Kinase Inhibitors in Multiple Myeloma. Blood. 2007;110(11):274B, Abstract 4804.
National Institute of Health, Cancer. MedlinePlus. Retrieved online at: http://www.nlm.nih.gov/medlineplus/cancer.html. 10 pages. Apr. 16, 2007.
O'Donnell et al., Cancer pharmacoethnicity: ethnic differences in susceptibility to the effects of chemotherapy. Clin Cancer Res. Aug. 1, 2009;15(15):4806-14.
O'Reilly et al., Urinary Soluble CD163 in Active Renal Vasculitis. J Am Soc Nephrol. Sep. 2016;27(9):2906-16.
Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.
Ocio et al., In vitro and in vivo rationale for the triple combination of panobinostat (LBH589) and dexamethasone with either bortezomib or lenalidomide in multiple myeloma. Haematologica. May 2010;95(5):794-803.
Ocio et al., Phase I study of plitidepsin in combination with bortezomib and dexamethasone in patients with relapsed and/or refractory multiple myeloma. Journal of Clinical Oncology. 2016;34:Abstract 8006, 1 page.
Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110:Abstract 1514. ASH Annual Meeting.
Ocio, Epigenetic regulation and HAC inhibitors, Still a role for these agents in MM? Institute of Biomedical Research of Salamanca, University of Salamanca, Cancer Research Center, Slideshow. 32 pages, (2016).
Offidani et al., Efficacy and tolerability of bendamustine, bortezomib and dexamethasone in patients with relapsed-refractory multiple myeloma: a phase II study. Blood Cancer J. Nov. 22, 2013;3:e162.
Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.
Oi et al., Synergistic induction of NY-ESO-1 antigen expression by a novel histone deacetylase inhibitor, valproic acid, with 5-aza-2'-deoxycytidine in glioma cells. J Neurooncol. Mar. 2009;92(1):15-22.
Oken et al., Toxicity and response criteria of the Eastern Cooperative Oncology Group. Am J Clin Oncol. Dec. 1982;5(6):649-55.

(56) References Cited

OTHER PUBLICATIONS

Oriol et al., Outcome after relapse of acute lymphoblastic leukemia in adult patients included in four consecutive risk-adapted trials by the PETHEMA Study Group. Haematologica. Apr. 2010;95(4):589-596.
Paris et al., Histone deacetylase inhibitors: from bench to clinic. J Med Chem. Mar. 27, 2008;51(6):1505-29.
Phan et al., An update on ethnic differences in drug metabolism and toxicity from anti-cancer drugs. Expert Opin Drug Metab Toxicol. Nov. 2011;7(11):1395-410.
Phiel et al., Histone deacetylase is a direct target of valproic acid, a potent anticonvulsant, mood stabilizer, and teratogen. J Biol Chem. Sep. 28, 2001;276(39):36734-41.
Pitha et al., Parenteral hydroxypropyl cyclodextrins: intravenous and intracerebral administration of lipophiles. J Pharm Sci. Jun. 1994;83(6):833-7.
Poenisch et al., Bendamustine/Prednisone Versus Melphalane/Prednisone in the Primary Treatment of Multiple Myeloma: an Updated Analysis of the 94BP01 Protocol. Blood. 2000;96(Suppl 1:759a), Abstract 3284, Poster Board Session 748-111.
Puetzer et al., Towards novel strategies of targeting specific vulnerabilities of T-PLL cells. AACR Annual Meeting. Jul. 2017;77(Suppl 13), Abstract 1372.
Pönisch et al., Combined bendamustine, prednisone and bortezomib (BPV) in patients with relapsed or refractory multiple myeloma. J Cancer Res Clin Oncol. Mar. 2013;139(3):499-508.
Pönisch et al., Treatment of bendamustine and prednisone in patients with newly diagnosed multiple myeloma results in superior complete response rate, prolonged time to treatment failure and improved quality of life compared to treatment with melphalan and prednisone—a randomized phase III study of the East German Study Group of Hematology and Oncology (OSHO). J Cancer Res Clin Oncol. Apr. 2006;132(4):205-12.
Qian et al., Activity of PXD101, a histone deacetylase inhibitor, in preclinical ovarian cancer studies. Mol Cancer Ther. Aug. 2006;5(8):2086-95.
Rajewski et al., Preliminary safety evaluation of parenterally administered sulfoalkyl ether beta-cyclodextrin derivatives. J Pharm Sci. Aug. 1995;84(8):927-32.
Rang et al., Glucocorticoids. Rang and Dale's Pharmacology, Sixth Edition. Elsevier, Limited, 3 pages, (2007).
Rang et al., Rang and Dale's Pharmacology, Sixth Edition. Churchill Livingstone Elsevier. Chapter 51, p. 729, (2007).
Rasheed et al., Histone deacetylase inhibitors in cancer therapy. Expert Opin Investig Drugs. May 2007;16(5):659-78.
Rasschaert et al., A phase I study of bendamustine hydrochloride administered day 1+2 every 3 weeks in patients with solid tumours. Br J Cancer. Jun. 4, 2007;96(11):1692-8.
Rasschaert et al., A phase I study of bendamustine hydrochloride administered once every 3 weeks in patients with solid tumors. Anticancer Drugs. Jun. 2007;18(5):587-95.
Reagan-Shaw et al., Dose translation from animal to human studies revisited. FASEB J. Mar. 2008;22(3):659-61.
Regna et al., HDAC expression and activity is upregulated in diseased lupus-prone mice. Int Immunopharmacol. Dec. 2015;29(2):494-503.
Reilly et al., Modulation of renal disease in MRL/lpr mice by suberoylanilide hydroxamic acid. J Immunol. Sep. 15, 2004;173(6):4171-8.
Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.
Richardson et al., PANORAMA 2: panobinostat in combination with bortezomib and dexamethasone in patients with relapsed and bortezomib-refractory myeloma. Blood. Oct. 3, 2013;122(14):2331-7.
Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).
Ryu et al., Valproic acid downregulates the expression of MGMT and sensitizes temozolomide-resistant glioma cells. J Biomed Biotechnol. 2012;2012:987495. 9 pages.
Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.
Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.
Santacruz et al., The prognostic impact of minimal residual disease in patients with chronic lymphocytic leukemia requiring first-line therapy. Haematologica. May 2014;99(5):873-80.
Sarkaria et al., Mechanisms of chemoresistance to alkylating agents in malignant glioma. Clin Cancer Res. May 15, 2008;14(10):2900-8.
Saulnier et al., An Efficient Method for the Synthesis of Guanidino Prodrugs. Bioorganic & Medicinal Chemistry Letters. 1994;4(16):1985-1990.
Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.
Schöffski et al., Repeated administration of short infusions of bendamustine: a phase I study in patients with advanced progressive solid tumours. J Cancer Res Clin Oncol. Jan. 2000;126(1):41-7.
Schöffski et al., Weekly administration of bendamustine: a phase I study in patients with advanced progressive solid tumours. Ann Oncol. Jun. 2000;11(6):729-34.
Serra et al., Co-clinical trial of olaparib in breast and ovarian patient-derived tumor xenografts (PDX) enables the identification of response biomarkers. Clin Cancer Res. 2016;22(Suppl 16):Abstract B02, 4 pages.
Shah et al., Comprehensive analysis of MGMT promoter methylation: correlation with MGMT expression and clinical response in GBM. PLoS One. Jan. 7, 2011;6(1):e16146.
Shipley et al., Acute myelogenous leukemia. Exp Hematol. Jun. 2009;37(6):649-58.
Siegel et al., Vorinostat in combination with lenalidomide and dexamethasone in patients with relapsed or refractory multiple myeloma. Blood Cancer J. Feb. 21, 2014;4(2):e182, 6 pages.
Simon, Optimal two-stage designs for phase II clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Sturn et al., Genesis: cluster analysis of microarray data. Bioinformatics. Jan. 2002;18(1):207-8.
Tago et al., Repeated 0.5-Gy gamma irradiation attenuates autoimmune disease in MRL-lpr/lpr mice with suppression of CD3+CD4−CD8−220+ T-cell proliferation and with up-regulation of CD4+CD25+Foxp3+ regulatory T cells. Radiat Res. Jan. 2008;169(1):59-66.
Takai et al., Human ovarian carcinoma cells: histone deacetylase inhibitors exhibit antiproliferative activity and potently induce apoptosis. Cancer. Dec. 15, 2004;101(12):2760-70.
Tesar et al., Limitations of standard immunosuppressive treatment in ANCA-associated vasculitis and lupus nephritis. Nephron Clin Pract. 2014;128(3-4):205-15.
Thurn et al., Rational therapeutic combinations with histone deacetylase inhibitors for the treatment of cancer. Future Oncol. Feb. 2011;7(2):263-83.

(56) References Cited

OTHER PUBLICATIONS

Topalian et al., Immune checkpoint blockade: a common denominator approach to cancer therapy. Cancer Cell. Apr. 13, 2015;27(4):450-61.
Trivedi et al., Management of Chemotherapy-Induced Peripheral Neuropathy. American Journal of Hematology / Oncology. Jan. 2015;11(1):4-10.
Tsai et al., Valproic Acid Enhanced Temozolomide-Induced Anticancer Activity in Human Glioma Through the p53-Puma Apoptosis Pathway. Front Oncol. Oct. 1, 2021;11:722754, 13 pages.
Tseng et al., A comparison of the molecular subtypes of triple-negative breast cancer among non-Asian and Taiwanese women. Breast Cancer Res Treat. Jun. 2017;163(2):241-254.
Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Van Krieken, New developments in the pathology of malignant lymphoma. A review of the literature published from Jan.-Apr. 2016. J Hematop. Jun. 13, 2016;9(2):73-83.
Viel et al., Optimizing glioblastoma temozolomide chemotherapy employing lentiviral-based anti-MGMT shRNA technology. Mol Ther. Mar. 2013;21(3):570-9.
Vippagunta et al., Crystalline Solids. Advanced Drug Delivery Reviews. 2001;48:3-26.
Vlachostergios et al., Bortezomib downregulates MGMT expression in T98G glioblastoma cells. Cell Mol Neurobiol. Apr. 2013;33(3):313-8.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Vyas et al., Cyclodextrin based novel drug delivery systems. J Incl Phenom Macrocycl Chem. 2008;62:23-42.
Wang et al., Effect of histone deacetylase inhibitor NL101 on rat neurons. Zhejiang Da Xue Bao Yi Xue Ban. May 2014;43(3):265-272. Abstract Only. 2 pages.
Wang et al., Independent validation of a model using cell line chemosensitivity to predict response to therapy. J Natl Cancer Inst. Sep. 4, 2013;105(17):1284-91.
Wang et al., Phase 1 trial of linifanib (ABT-869) in patients with refractory or relapsed acute myeloid leukemia. Leuk Lymphoma. Aug. 2012;53(8):1543-51.
Wang et al., Toward selective histone deacetylase inhibitor design: homology modeling, docking studies, and molecular dynamics simulations of human class I histone deacetylases. J Med Chem. Nov. 3, 2005;48(22):6936-47.
Watanabe et al., Modulation of renal disease in MRL/lpr mice genetically deficient in the alternative complement pathway factor B. J Immunol. Jan. 15, 2000;164(2):786-94.
Weil et al., Breast cancer metastasis to the central nervous system. Am J Pathol. Oct. 2005;167(4):913-20.
Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.
Wikipedia, Triple-negative breast cancer. Retrieved online at: https://en.wikipedia.org/wiki/Triple-negative_breast_cancer. 7 pages, Feb. 20, 2017.
Wilson et al., Histone deacetylase 3 (HDAC3) and other class I HDACs regulate colon cell maturation and p21 expression and are deregulated in human colon cancer. J Biol Chem. May 12, 2006;281(19):13548-58.
Wilson et al., Relationship of p53, bcl-2, and tumor proliferation to clinical drug resistance in non-Hodgkin's lymphomas. Blood. Jan. 15, 1997;89(2):601-9.
Witzel et al., Long-term tumor remission under trastuzumab treatment for HER2 positive metastatic breast cancer—results from the HER-OS patient registry. BMC Cancer. Nov. 4, 2014;14:806. 7 pages.
Xiao et al., Antineutrophil cytoplasmic autoantibodies specific for myeloperoxidase cause glomerulonephritis and vasculitis in mice. J Clin Invest. Oct. 2002;110(7):955-63.
Xie et al., Quantitative structure-activity relationship study of histone deacetylase inhibitors. Curr Med Chem Anticancer Agents. May 2004;4(3):273-99.
Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.
Yardley, Drug resistance and the role of combination chemotherapy in improving patient outcomes. Int J Breast Cancer. 2013;2013:137414. 15 pages.
Zaja et al., Bendamustine salvage therapy for T cell neoplasms. Ann Hematol. Sep. 2013;92(9):1249-54.
Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.
Zhao et al., Comparison of methods for evaluating drug-drug interaction. Front Biosci (Elite Ed). Jan. 1, 2010;2:241-9.
Zhu et al., Histone deacetylase 3 implicated in the pathogenesis of children glioma by promoting glioma cell proliferation and migration. Brain Res. Jul. 3, 2013;1520:15-22.
Zinzani et al., Brentuximab Vedotin in Transplant-Naïve Relapsed/Refractory Hodgkin Lymphoma: Experience in 30 Patients. Oncologist. Dec. 2015;20(12):1413-6.
Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy.dose.escalation.of.tinostamustine.in.patients.with.relapsed.html?f=listing=3*browseby=8*sortby=1*media=1. 1 page, poster presentation. Jun. 1, 2019.
Zulkowski et al., Regression of brain metastases from breast carcinoma after chemotherapy with bendamustine. J Cancer Res Clin Oncol. Feb. 2002;128(2):111-3.

* cited by examiner

TINOSTAMUSTINE FOR USE IN TREATING SARCOMA

TECHNICAL FIELD

The present invention relates to methods of treating cancer, particularly sarcomas.

BACKGROUND OF THE INVENTION

Cancer is one of the most life threatening diseases. Cancer is a condition in which cells in a part of the body experience out-of-control growth. According to latest data from American Cancer Society, it is estimated there will be 1.69 million new cases of cancer in USA in 2017. Cancer is the second leading cause of death in the United States (second only to heart disease) and will claim more than 601,000 lives in 2017. In fact, it is estimated the average lifetime risk of developing cancer is 40.8% for American males and 37.5% for American women. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

For decades surgery, chemotherapy, and radiation were the established treatments for various cancers. Patients usually receive a combination of these treatments depending upon the type and extent of their disease. But chemotherapy is the most important option for cancer patients when surgical treatment (i.e. the removal of diseased tissue) is impossible. While surgery is sometimes effective in removing tumours located at certain sites, for example, in the breast, colon, and skin, it cannot be used in the treatment of tumours located in other areas, such as the backbone, nor in the treatment of disseminated hematological cancers including cancers of the blood and blood-forming tissues (such as the bone marrow). Such cancers include multiple myeloma, lymphoma and leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in chemotherapy is the development of drug resistance by the cancer cells, a serious problem that may lead to recurrence of disease or even death. Thus, more effective cancer treatments are needed.

Solid tumours are an abnormal mass of tissue that usually does not contain cysts or liquid areas. Solid tumours may be benign (not cancer), or malignant (cancer). Different types of solid tumours are named for the type of cells that form them. Examples of solid tumours are carcinomas and sarcomas. The four most common cancers occurring worldwide are all solid tumours, namely lung, breast, bowel and prostate cancer. These four solid tumour cancers account for around 4 in 10 of all cancers diagnosed worldwide.

However, not all solid tumours are as common. Sarcomas are rare cancers that can develop in almost any part of the body, including muscle, bone, nerves, cartilage, tendons, blood vessels and the fatty and fibrous tissues. There are three main types of sarcoma: soft tissue sarcoma, bone sarcoma and gastrointestinal stromal tumours (GIST) and in the US, around 20,000 new sarcomas are diagnosed each year. The overall relative 5-year survival rate of people with soft tissue sarcomas is around 50% according to statistics from the National Cancer Institute (NCI).

There is therefore a need for new effective chemotherapeutic treatments.

In WO-A-2010/085377, the compound of formula I below is disclosed. It is a first-in-class dual-functional alkylating-HDACi fusion molecule which potently inhibits HDAC-regulated pathways.

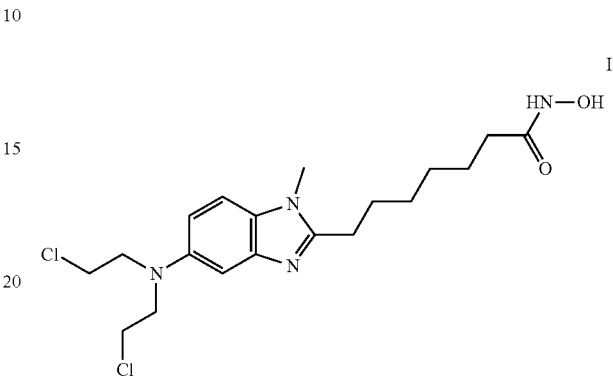

Biological assays showed that the compound of formula I potently inhibits HDAC enzyme (HDAC1 $IC_{50}$ of 9 nM). The compound of formula I has an INN of tinostamustine and is also known in the art as EDO-S101. It is an AK-DAC (a first-in-class alkylating deacetylase molecule) that, in preclinical studies, has been shown to simultaneously improve access to the DNA strands within cancer cells, break them and block damage repair.

SUMMARY OF THE INVENTION

In a first aspect of the present invention there is provided tinostamustine or a pharmaceutically acceptable salt thereof for use in the treatment of sarcoma in a patient in need thereof selected from soft tissue sarcoma, bone sarcoma or non-KIT gastrointestinal stromal tumour (GIST).

It has surprisingly been discovered that tinostamustine or a pharmaceutically acceptable salt thereof is particularly effective in the treatment of sarcoma, with activity data showing strong sensitivity to this compound. Thus, the need for a new and effective treatment of sarcoma is met by the present invention.

In a further aspect of the present invention there is provided the use of tinostamustine or a pharmaceutically acceptable salt thereof in the manufacture of a medicament for the treatment of sarcoma selected from soft tissue sarcoma, bone sarcoma or non-KIT gastrointestinal stromal tumour (GIST).

In a further aspect of the present invention there is provided a method of treating sarcoma selected from soft tissue sarcoma, bone sarcoma or non-KIT gastrointestinal stromal tumour (GIST), in a patient in need thereof comprising administering to said patient an effective amount of tinostamustine or a pharmaceutically acceptable salt thereof.

In a further aspect of the present invention there is provided a kit comprising tinostamustine or a pharmaceutically acceptable salt thereof together with instructions for treating sarcoma selected from soft tissue sarcoma, bone sarcoma or non-KIT gastrointestinal stromal tumour (GIST).

The following features apply to all aspects of the invention.

The sarcoma may be a soft tissue sarcoma.
The sarcoma may be a bone sarcoma.
The sarcoma may be from the Ewing family of tumours. The sarcoma may be Ewing tumour of bone. The sarcoma may be an extraosseous Ewing tumour. The sarcoma may start in the bone. The sarcoma may start in the soft tissue. The sarcoma may be primitive neuroectodermal tumour (PNET).

The sarcoma may be liposarcoma. The liposarcoma may be well-differentiated liposarcoma.

The liposarcoma may be myxoid liposarcoma. The liposarcoma may be pleomorphic liposarcoma. The liposarcoma may be dedifferentiated liposarcoma. Preferably the liposarcoma may be dedifferentiated liposarcoma.

The sarcoma may be non-KIT GIST.
The sarcoma may be wildtype GIST.
The sarcoma may be paediatric GIST.
The sarcoma may be relapsed and/or refractory.
The sarcoma may be localized.
The sarcoma may be metastatic.
The sarcoma may be advanced.
The sarcoma may have progressed after at least one line of standard therapy.

DETAILED DESCRIPTION OF THE INVENTION

Figure 1:
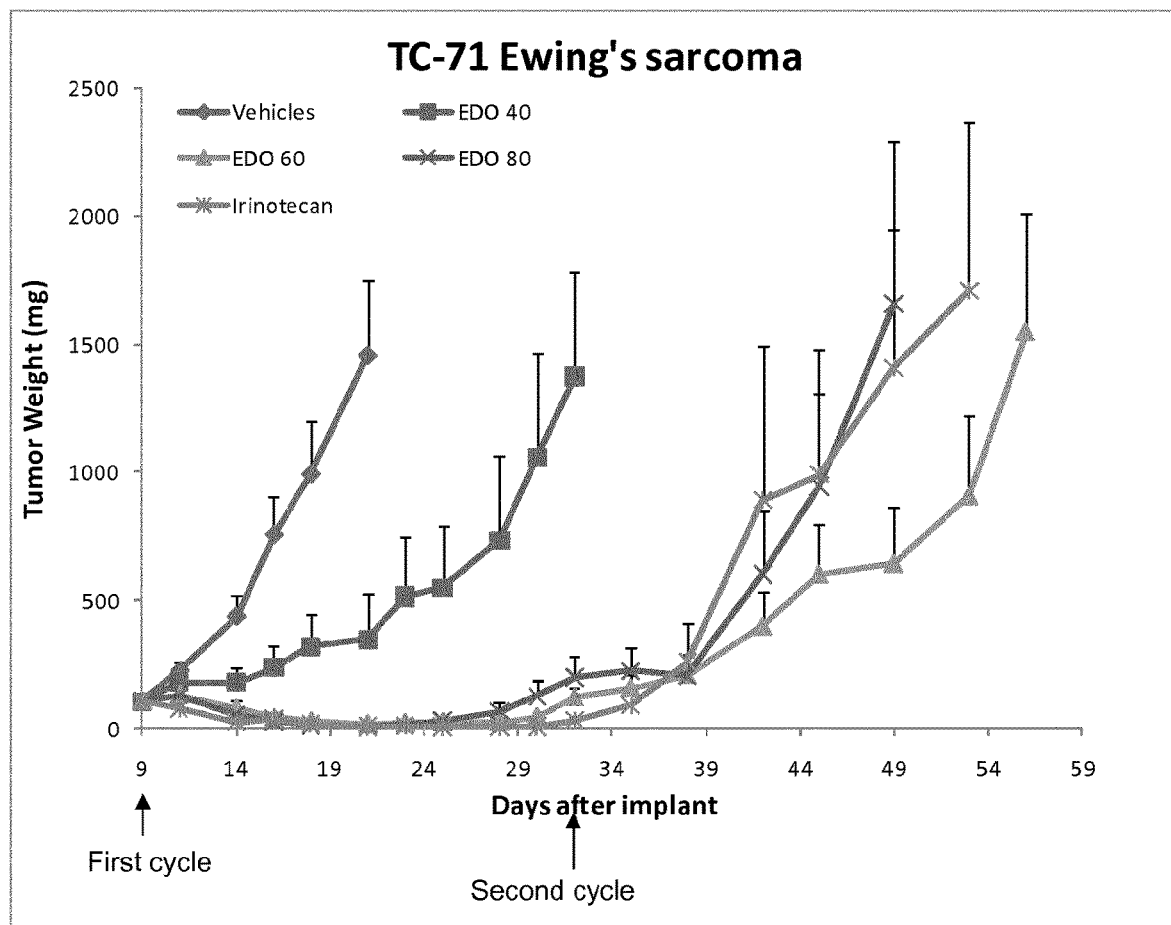
FIG. 1 shows the antitumoural activity of EDO-S101 against TC-71 Ewing sarcoma.

In the present application, a number of general terms and phrases are used, which should be interpreted as follows.

The compound of formula I has an INN of tinostamustine and is also known in the art as EDO-S101. The IUPAC name is 7-(5-(bis(2-chloroethyl)amino)-1-methyl-1H-benzo[d]imidazol-2-yl)-N-hydroxyheptanamide.

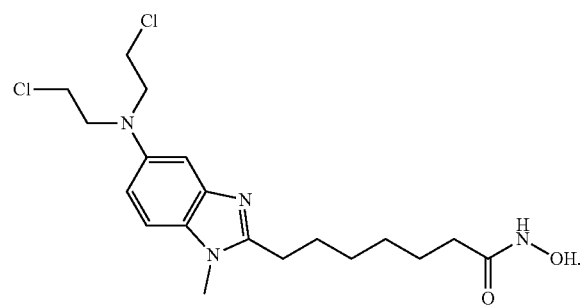

I

"Patient" includes humans, non-human mammals (e.g., dogs, cats, rabbits, cattle, horses, sheep, goats, swine, deer, and the like) and non-mammals (e.g., birds, and the like).

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonae, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

In the present invention, the pharmaceutically acceptable salt of tinostamustine may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate salt.

It has surprisingly been found that tinostamustine or a pharmaceutically acceptable salt thereof shows surprising efficacy in solid tumours. In particular, it has been found that tinostamustine or a pharmaceutically acceptable salt thereof is useful in the treatment of sarcomas.

Sarcomas are rare cancers that develop in the muscle, bone, nerves, cartilage, tendons, blood vessels and the fatty and fibrous tissues. They can affect almost any part of the body, on the inside or the outside. Sarcomas commonly affect the arms, legs and trunk. They also appear in the stomach and intestines as well as behind the abdomen (retroperitoneal sarcomas) and the female reproductive system (gynaecological sarcomas).

Bone sarcomas affect less than 500 people in the UK each year, making it a very rare form of cancer. Not all bone cancers will be sarcomas.

Soft tissue sarcomas can affect any part of the body. They develop in supporting or connective tissue such as the muscle, nerves, fatty tissue, and blood vessels. Soft tissue sarcomas include: GIST which is a common type of sarcoma which develops in the gastrointestinal (GI) tract; gynaecological sarcomas which occur in the female reproductive system: the uterus (womb), ovaries, vagina, vulva and fallopian tubes; and retroperitoneal sarcomas which occur in the retroperitoneum.

Unless detected at an early stage when the tumour can be removed by surgery there is currently no cure for soft tissue sarcoma. Approximately 16% of patients with soft tissue sarcoma have advanced stage (metastatic) disease. For these patients, the relative 5 year survival rate is 16% (American Cancer Society).

Liposarcoma

One particular soft tissue sarcoma is liposarcoma. Liposarcoma is a rare cancer of connective tissues that resemble fat cells under a microscope. It accounts for up to 18% of all soft tissue sarcomas. Liposarcoma can occur in almost any part of the body, but more than half of liposarcoma cases involve the thigh, and up to a third involve the abdominal cavity. Liposarcoma tends to affects adults between the ages of 40 and 60. When it does occur in children, it is usually during the teenage years. There are four types of liposarcoma as shown below. The risk of recurrence and metastasis with liposarcoma increases with higher grade.

Well-differentiated liposarcoma is the most common subtype and usually starts as a low grade tumour. Low grade tumour cells look much like normal fat cells under the microscope and tend to grow and change slowly.

Myxoid liposarcoma is an intermediate to high grade tumour. Its cells look less normal under the microscope and may have a high grade component.

Pleomorphic liposarcoma is the rarest subtype and is a high grade tumour with cells that look very different from normal cells.

Dedifferentiated liposarcoma occurs when a low grade tumour changes, and the newer cells in the tumour are high grade.

Ewing Family of Tumours

The Ewing family of tumours is a group of cancers that start in the bones or nearby soft tissues that share some common features. These tumours can develop at any age, but they are most common in the early teen years. The main types of Ewing tumours are:

Ewing sarcoma of bone: Ewing sarcoma that starts in a bone is the most common tumour in this family. This type of tumour was first described by Dr. James Ewing in 1921, who found it was different from the more common bone tumour, osteosarcoma. Seen under a microscope, its cells looked different from osteosarcoma cells. It was also more likely to respond to radiation therapy.

Extraosseous Ewing tumour (EOE): Extraosseous Ewing tumours start in soft tissues around bones, but they look and act very much like Ewing sarcomas in bones. They are also known as extraskeletal Ewing sarcomas.

Primitive neuroectodermal tumour (PNET): This rare childhood cancer also starts in bone or soft tissue and shares many features with Ewing sarcoma of bone and EOE. PNETs that start in the chest wall are known as Askin tumours. PNETs that start in the bone are known as peripheral neuroectodermal sarcoma of bone.

The cells that make up Ewing sarcoma, EOE, and PNET are very similar. They tend to have the same DNA (gene) abnormalities and share similar proteins, which are rarely found in other types of cancers. The three cancers are thought to develop from the same type of cells and while there are differences among these tumours, they are all currently treated in the same way.

Most Ewing tumours occur in the bones. The most common sites are: the pelvis (hip bones), the chest wall (such as the ribs or shoulder blades), or the legs, mainly in the middle of the long bones. Extraosseous Ewing tumours can occur almost anywhere.

Most Ewing tumours occur in children and teens, but they can also occur in adults.

Gastrointestinal Stromal Tumours (GISTs)

A further type of soft tissue sarcomas are gastrointestinal stromal tumours (GISTs). GISTs are uncommon tumours of the gastrointestinal (GI) tract. Although they comprise fewer than 1% of all GI tumours, GIST are the most common mesenchymal tumours of the GI tract. According to the National Cancer Institute, it has been estimated that there are 3,300 to 6,000 new GIST cases per year in the United States. A study based on Surveillance, Epidemiology and End Results (SEER) registry data found that the age-adjusted yearly incidence of GIST in the United States was 6.8 per million from 1992 to 2000. However, the true incidence is not known, in part because many tumours have not been tested for the characteristic KIT (CD117) or platelet-derived growth factor receptor alpha (PDGFRA) gene mutations. In addition, small, indolent GIST, only a few millimeters in diameter, are common in the general population and are not included in cancer registries. GIST are equally distributed across all geographic and ethnic groups and men and women are equally affected. Most patients present between the ages of 50 and 80. The vast majority of GIST are sporadic, but there are rare familial forms associated with the characteristic heritable mutations in the KIT gene (or, rarely, in succinate dehydrogenase genes in Carney-Stratakis syndrome). Familial GIST may present as multiple primary tumours.

GIST can occur anywhere along the GI tract, but most often are found in the stomach or small intestine. The American Joint Committee on Cancer (AJCC) Cancer Staging Manual lists the following approximate distributions: stomach (60%); small intestine (30%); rectum (3%); colon (1-2%); esophagus (<1%); omentum/mesentery (rare).

Less frequently, GIST may arise in the appendix, gallbladder, pancreas, retroperitoneum, and paravaginal and periprostatic tissues. Approximately 20% to 25% of gastric GIST and 40% to 50% of small intestinal GIST are clinically aggressive. It has been estimated that approximately 10% to 25% of patients present with metastatic disease.

The clinical presentation of patients with GIST varies depending on the anatomic location of the tumour and the tumour size and aggressiveness. The most common presentation of GIST is GI bleeding, which may be acute (melena or hematemesis) or chronic and results in anemia.

Smaller lesions may be incidental findings during surgery, radiologic studies, or endoscopy. The natural history of these incidental tumours and the frequency of progression to symptomatic disease are unknown. There may be a substantial reservoir of small GIST tumours that do not progress to symptomatic stages. For example, a series of 98 consecutive systematic autopsies on adults who died of unrelated causes revealed grossly recognizable gastric tumours (1 mm-6 mm) that were histologically diagnosed as GIST in 22.5% of cases. Sufficient DNA was available for analysis in 26 patients, revealing 13 patients with mutations in KIT exon 11 and one in PDGFRA.

In a retrospective study of 200 GIST cases, typical clinical manifestations of malignancy included liver metastases and/or dissemination within the abdominal cavity. Lymph node involvement and spread to the lungs or other extra-abdominal sites was unusual. Advanced disease may be associated with metastases to distant sites, including lung and bone. Brain metastases are rare.

Typically arising within the muscle wall of the GI tract, GIST range in size from less than 1 cm to more than 40 cm, with an average size of approximately 5 cm when diagnosed clinically.[2] Small GIST may form solid subserosal, intramural, or, less frequently, polypoid intraluminal masses. Large tumours tend to form external masses attached to the outer aspect of the gut involving the muscular layers. GIST morphology is quite varied; the tumours are composed of the following: spindle cells (70%); epithelioid cells (20%); and mixed spindle and epithelioid cells (10%).

GIST encompass a broad continuum of histologic patterns, ranging from bland-appearing tumours with very low mitotic activity (often previously designated leiomyomas) to very aggressive-appearing patterns (previously often called leiomyosarcomas). They may originate from interstitial cells of Cajal (ICC) or their stem cell-like precursors, although this is not certain.

The most commonly used marker for GIST is the CD117 antigen, a marker expressed by ICC. Approximately 95% of GISTs are positive for the CD117 antigen, an epitope of the KIT receptor tyrosine kinase. However, CD117 immunohistochemistry is not specific for GIST, as weak reactivity occurs with other mesenchymal neoplasms; accordingly, morphologic examination and the use of other immunostains in difficult cases are indispensable. In addition, false-positive CD117 staining can occur if antigen retrieval techniques are used in the pathology laboratory to enhance marker expression.

Approximately 85% of GIST contain oncogenic mutations in one of two receptor tyrosine kinases: KIT or PDGFRA (platelet-derived growth factor receptor alpha). Constitutive activation of either of these receptor tyrosine kinases plays a central role in the pathogenesis of GIST. Wild-type tumours, with no detectable KIT or PDGFRA mutations, account for 12% to 15% of all GIST. Fewer than 5% of GIST occur in the setting of syndromic diseases, such as neurofibromatosis type 1 (NF1), Carney triad syndrome, and other familial diseases. The correct identification of GIST is important because of the availability of specific, molecular-targeted therapy with KIT/PDGFRA tyrosine kinase inhibitors (TKI) such as imatinib mesylate or, in the case of imatinib-resistant GIST, sunitinib malate.

Wild-type or non-KIT GIST represents an even narrower sub-set of GIST patients that do not respond as well to current therapies. As discussed above, GIST typically presents in patients aged 50 to 80. Pediatric GIST is therefore rare but it has been suggested that the biology of pediatric GIST is different from adult GIST. For example, patients with pediatric GIST are predominantly female, their tumours are of epithelioid or mixed histology, they lack large-scale chromosomal aberrations, and only rarely (<15%) do they have KIT or PDGFRA mutations. As such, paediatric GIST typically is non-KIT.

Compared to other intra-abdominal sarcomas, survival in GIST patients after surgery alone is favorable. In a retrospective study involving 200 patients that predated the use of TKI, the 5-year disease-specific survival rate for GIST patients with primary disease who underwent complete resection of gross disease (N=80) was 54%, with survival predicted by tumour size; the overall disease-specific survival was 35% at 5 years. Other studies, which also predated TKI, reported 5-year survival rates of 40% to 63% for patients undergoing complete resections of GIST.

The median disease-specific survival of patients with metastatic GIST (N=94) was 19 months. In one retrospective study involving 119 patients with metastatic GIST, it was found that once a GIST becomes metastatic, kinase genotype did not factor into overall survival. The median time to recurrence for patients on imatinib is 2 years.

The therapeutically effective amount of tinostamustine or a pharmaceutically acceptable salt administered to the patient is an amount which confers a therapeutic effect in accordance with the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of tinostamustine or a pharmaceutically acceptable salt thereof according to the present invention is believed to be one wherein tinostamustine or a pharmaceutically acceptable salt thereof is included at a dosage range of from 0.3 mg/m$^2$ to 300 mg/m$^2$ body surface area of the patient or from 60 mg/m$^2$ to 150 mg/m$^2$ body surface area of the patient. In a preferred embodiment, the dosage range is from 80 to 100 mg/m$^2$ body surface area of the patient.

The specific therapeutically effective dose level for any particular patient will depend upon a variety of factors including the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

"Metastatic Cancer". Cancer has the ability to spread within the body. Cancer cells can spread locally by moving into nearby normal tissue. Cancer can also spread regionally, to nearby lymph nodes, tissues, or organs. Cancer can therefore spread to distant parts of the body. When this happens, it is called metastatic cancer (also known as stage IV cancer), and the process by which cancer cells spread to other parts of the body is called metastasis. Thus, in metastasis, cancer cells break away from where they first formed (primary cancer), travel through the blood or lymph system, and form new tumours (metastatic tumours) in other parts of the body.

Metastatic cancer cells have features like that of the primary cancer and not like the cells in the place where the cancer is found. This enables doctors to tell whether a cancer is metastatic. Metastatic cancers are given the same name as the primary cancer. For example, breast cancer that has spread to the lung is called metastatic breast cancer, not lung cancer. It is treated as stage IV breast cancer, not as lung cancer.

Metastatic sarcoma (for example metastatic soft tissue sarcoma, metastatic bone sarcoma or metastatic non-KIT gastrointestinal stromal tumour (GIST) refers to a sarcoma that has metastasised to a new location in the body. The cancer is treated as a stage IV sarcoma (for example a stage IV soft tissue sarcoma, a stage IV bone sarcoma or stage IV non-KIT GIST).

"Advanced Cancer" is a cancer that is not curable but responds to treatment. Disease directed therapy is still very important because it prolongs life. For terminal cancer, therapy cannot prolong survival significantly due to the progressive nature of the disease and palliative care is the main treatment option.

Suitable examples of the administration form of tinostamustine or a pharmaceutically acceptable salt thereof include without limitation oral, topical, parenteral, sublingual, rectal, vaginal, ocular, and intranasal. Parenteral administration includes subcutaneous injections, intravenous, intramuscular, intrasternal injection or infusion techniques. Preferably, tinostamustine or a pharmaceutically acceptable salt thereof is administered parenterally, and most preferably intravenously.

Preferably, tinostamustine or a pharmaceutically acceptable salt thereof is administered intravenously to the patient in need thereof at a dosage level to the patient in need thereof of from 0.3 mg/m$^2$ to 300 mg/m$^2$ body surface area of the patient.

Preferably, tinostamustine or a pharmaceutically acceptable salt thereof is administered intravenously to the patient in need thereof at a dosage level to the patient in need thereof of from 60 mg/m$^2$ to 150 mg/m$^2$ body surface area of the patient.

Preferably, tinostamustine or a pharmaceutically acceptable salt thereof is administered intravenously to the patient in need thereof at a dosage level to the patient in need thereof of from 80 mg/m$^2$ to 100 mg/m$^2$ body surface area of the patient.

It has been found that in embodiments of the present invention, tinostamustine or a pharmaceutically acceptable salt thereof or medicament comprising the same may preferably be administered to a patient in need thereof on days 1, 8 and 15 of a 28 day treatment cycle or on days 1 and 15 of a 28 day treatment cycle.

Preferably, tinostamustine or a pharmaceutically acceptable salt thereof is administered on days 1 and 15 of a 28 day treatment cycle.

It has been found that in embodiments of the present invention, tinostamustine or a pharmaceutically acceptable salt thereof or medicament comprising the same may preferably be administered to a patient in need thereof over an infusion time of 60 minutes; or an infusion time of 45 minutes; or an infusion time of 30 minutes.

Preferably, tinostamustine or a pharmaceutically acceptable salt thereof is administered over an infusion time of 60 minutes.

In a preferred embodiment, tinostamustine or a pharmaceutically acceptable salt is administered to the patient in need thereof at a dosage level of from 80 mg/m$^2$ to 100 mg/m$^2$ body surface area of the patient, on days 1 and 15 of a 28 day treatment cycle, over an infusion time of 60 minutes.

In embodiments of the present invention, there is provided a kit comprising tinostamustine or a pharmaceutically acceptable salt thereof or medicament comprising the same together with instructions.

The instructions may advise administering tinostamustine or a pharmaceutically acceptable salt thereof according to variables such as the state of the solid tumours being treated; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts.

In a further embodiment of the present invention, the patient in need of said treatment is given radiotherapy with (including prior to, during or after) treatment of the solid tumour(s) with tinostamustine or a pharmaceutically acceptable salt thereof. In embodiments of the present invention, the patient is treated with tinostamustine or a pharmaceutically acceptable salt thereof and radiotherapy. Preferably, the patient is given radiotherapy treatment prior to the treatment with tinostamustine or a pharmaceutically acceptable salt thereof. The radiotherapy may be given at a dose of 1 to 5 Gy over 5-10 consecutive days and preferably 2 Gy over 5-10 consecutive days.

In a further embodiment of the present invention, the patient in need of said treatment is given radiotherapy prior to or after treatment of the solid tumours with tinostamustine or a pharmaceutically acceptable salt thereof. Preferably, the patient is given radiotherapy treatment prior to the treatment with tinostamustine or a pharmaceutically acceptable salt thereof. The radiotherapy may be given at a dose of 1 to 5 Gy over 5-10 consecutive days and preferably 2 Gy over 5-10 consecutive days.

When intended for oral administration, tinostamustine or a pharmaceutically acceptable salt thereof or medicament comprising the same may be in solid or liquid form, where semi-solid, semi-liquid, suspension and gel forms are included within the forms considered herein as either solid or liquid.

Tinostamustine or a pharmaceutically acceptable salt thereof or medicament comprising the same can be prepared for administration using methodology well known in the pharmaceutical art. Examples of suitable pharmaceutical formulations and carriers are described in "Remington's Pharmaceutical Sciences" by E. W. Martin.

As a solid composition for oral administration, tinostamustine or a pharmaceutically acceptable salt thereof can be formulated into a powder, granule, compressed tablet, pill, capsule, chewing gum, wafer or the like form. Such a solid composition typically contains one or more inert diluents or carriers. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When tinostamustine or a pharmaceutically acceptable salt thereof compositions is in the form of a capsule (e.g. a gelatin capsule), it can contain, in addition to materials of the above type, a liquid carrier such as polyethylene glycol, cyclodextrin or a fatty oil.

Tinostamustine or a pharmaceutically acceptable salt thereof compositions can be in the form of a liquid, e.g. an elixir, syrup, solution, emulsion or suspension. The liquid can be useful for oral administration or for delivery by injection. When intended for oral administration, tinostamustine or a pharmaceutically acceptable salt thereof compositions can comprise one or more of a sweetening agent, preservatives, dye/colorant and flavor enhancer. In tinostamustine or a pharmaceutically acceptable salt thereof compositions for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, tinostamustine or a pharmaceutically acceptable salt thereof or medicament comprising the same is administered intravenously.

Liquid forms of tinostamustine or a pharmaceutically acceptable salt thereof or medicament comprising the same, may be solutions, suspensions or other like form, and can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

Tinostamustine or a pharmaceutically acceptable salt thereof or medicament comprising the same can be administered by any convenient route, for example by infusion or bolus injection, by absorption through epithelial or mucocutaneous linings, and preferably by bolus.

Examples of compositions comprising tinostamustine or a pharmaceutically acceptable salt thereof are disclosed in WO2013/040286.

The present invention may be further understood by consideration of the following non-limiting examples.

EXAMPLES

In the following examples, tinostamustine is referred to as EDO-S101 and has the following formula:

I

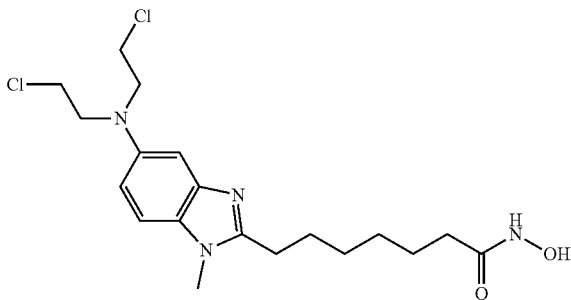

EDO-S101 may be prepared as described in Example 6 of WO-A-2010/085377.

Materials and Methods

Antitumour Activity of EDO-S101 Against Different Xenograft Models of Human Soft Tissue Sarcoma EDO-S101 and Control Compounds EDO-S101 was provided by EDO MundiPharma, and synthesised as described in Example 6 of WO-A-2010/085377.
Irinotecan was purchased from Actavis.
Doxorubicin was purchased from Sigma-Aldrich, St. Louis, Mo.

Test System: Mice

Experiments were performed with female Athymic nude mice, 9-10 weeks old obtained from Harlan Laboratories (Udine, Italy). They were maintained under Specific Pathogen Free conditions with constant temperature and humidity, according to the institutional guidelines. Mice were identified by ear tag.

Study Groups and Treatment Regimens

Study groups are listed below (at least eight mice for each group):
Vehicles
EDO-S101 80 mg/kg i.v. single dose
EDO-S101 60 mg/kg i.v. once a week per three weeks (q7dx3, one week observation time followed by an eventual subsequent cycle)
EDO-S101 40 mg/kg i.v. once a week per three weeks (q7dx3, one week observation time followed by an eventual subsequent cycle)
Irinotecan (TC-71 model) or Doxorubicin (DD013 model)
EDO-S101 was administered i.v. in a volume of 10 ml/kg. Irinotecan 50 mg/kg was administered intravenously, once a week for three weeks, in a volume of 10 ml/kg. Doxorubicin 8 mg/kg was administered intravenously, once a week for two weeks, in a volume of 10 ml/kg.

Antitumour Activity and Drug Tolerability

Tumour growth mice was monitored two/three times a week (depending on tumour growth rate, to avoid unnecessary stress to the animals) by Vernier caliper. Mice were sacrificed when tumour reached a mean weight of 2±0.5 gr. The antitumour activity will be expressed as T/C %, where T and C were the mean tumour weight of treated and control groups, respectively. Mice were monitored daily and weighted at least two times a week. Tolerability was evaluated on the basis of body weight loss (BWL) and clinical observation.

Statistical Analysis

Statistical analysis was performed with GraphPad Prism version 6.01 software (GraphPad software, Inc., La Jolla, Calif., USA). ANOVA test was performed to evaluate if there were statistically significant differences between treated and control groups.

Example 1

Antitumour Activity and Drug Tolerability in TC-71 Ewing Sarcoma Model $5 \times 10^6$ TC-71 cells were inoculated subcutaneously in the right flank of mice. The growing tumour masses were measured with the aid of a Vernier caliper, and the tumour weights (1 mm$^3$=1 mg) were calculated by the formula: length×(width)$^2$/2. When tumour load achieved about 100 mg, mice were randomized into the experimental groups and treatment started.

FIG. 1 shows the antitumour activity of EDO-S101 administered at different doses and schedules to TC-71 bearing mice. Both EDO-S101 administered 80 mg/kg single dose and 60 mg/kg q7dx3 were extremely effective at reducing tumour growth with optimal T/C recorded on day 21 of 0.5% and 1%, for 80 mg/kg and 60 mg/kg doses respectively.

Treatment with EDO-S101 resulted in sustained tumour regressions in all of the treated mice with complete regressions (CR) in 4 out of 8 and 3 out of 8 mice in the 80 mg/kg and 60 mg/kg groups, respectively. The administration of a second cycle of treatments at both 80 and 60 mg/kg further delayed tumour re-growth without being able to arrest it. At the end of the experiment, one mouse in the group receiving 80 mg/kg and two mice in the 60 mg/kg group were still in CR.

EDO-S101 administered at 40 mg/kg q7dx3 was effective in arresting tumour growth compared to untreated tumours with an optimal T/C of 24% (day 21). Although treatment with EDO-S101 under this dose regimen resulted in a delay in tumour growth, no tumour regression in tumour volume was observed. The group treated with 40 mg/kg EDO-S101 were not administered a second dose cycle because of the tumour dimensions (mean TW 1055.5 mg on day 30).

Irinotecan was used as positive control. Administration of 50 mg/kg of Ironotecan q7dx3 to tumour-bearing mice resulted in tumour regression in all mice with 4 mice exhibiting sustained CR up to the conclusion of the experiment. The recorded optimal T/C was 0.4% on day 21.

Tumour weights for each animal and day are reported in Table 1. The statistical analysis is reported in Table 2.

The treatments with EDO-S101 40 mg/kg were well tolerated with a maximum BWL of 5.4% recorded on day 10, 24 h after the administration of the first dose. One mouse in the group was found dead for unknown reasons, probably not ascribable to the drug since all the other mice in the treatment group did not show signs of toxicity. In the group treated with 60 mg/kg EDO-S101, a maximum BWL of 11.7% was observed on day 25, 48 h after the administration of the third dose. The second cycle appeared to be well tolerated with BWL consistently <9% for all dose regimens. At the highest dose of 80 mg/kg of EDO-S101, a maximum body weight loss of 19.3% on day 14 was observed, 5 days after administration, indicating some dose-related toxicity. Nevertheless, the mice recovered within 10 days (day 24) and the second cycle was tolerated without significant body weight loss. Irinotecan 50 mg/kg was well tolerated with a maximum BWL of 7.5% recorded on day 25. Table 3 reports the body weights recorded throughout the experiment.

EDO-S101 was shown to be effective against Ewing sarcoma. A dose of 60 mg/kg EDO-S101, administered q7dx3 resulted to be the best choice both in terms of efficacy and tolerability.

TABLE 1

TC-71 tumour weight (mg) during the in vivo evaluation of EDO-S101 (treatments started on day 9).

| Vehicles # | Days from inoculum | | | | | |
|---|---|---|---|---|---|---|
| | 9 | 11 | 14 | 16 | 18 | 21 |
| 744 | 178.9 | 341.7 | 691.8 | 1415.0 | 2070.9 | 1965.7 |
| 702 | 149.6 | 316.3 | 615.0 | 667.8 | 851.4 | 1018.5 |
| 741 | 130.8 | 300.9 | 681.7 | 1105.6 | 1325.0 | 2596.4 |
| 756 | 102.1 | 158.4 | 177.5 | 258.9 | 234.3 | 286.0 |
| 711 | 93.9 | 260.3 | 552.7 | 1177.2 | 1360.1 | 2373.9 |
| 754 | 79.1 | 201.7 | 356.4 | 608.2 | 931.6 | 1524.5 |
| 719 | 56.8 | 142.7 | 262.9 | 519.4 | 767.0 | 1411.6 |
| 705 | 32.0 | 79.2 | 157.1 | 283.4 | 380.7 | 448.3 |
| mean | 102.9 | 225.2 | 436.9 | 754.4 | 990.1 | 1453.1 |
| se | 17.2 | 33.3 | 79.3 | 151.8 | 208.4 | 298.4 |

| EDO 80 # | Days from inoculum | | | | | | | | | | | | | | |
|---|---|---|---|---|---|---|---|---|---|---|---|---|---|---|---|
| | 9 | 11 | 14 | 16 | 18 | 21 | 23 | 25 | 28 | 30 | 32 | 35 | 38 | 42 | 45 | 49 |
| 710 | 222.4 | 369.7 | 209.5 | 124.6 | 68.6 | 23.4 | 16.8 | 38.4 | 117.5 | 220.0 | 340.2 | 319.1 | 239.8 | 598.5 | 790.9 | 1094.7 |
| 747 | 133.9 | 200.9 | 68.4 | 34.0 | 8.3 | 3.4 | 2.1 | 3.8 | 4.1 | 18.1 | 64.8 | 49.1 | 32.6 | 77.8 | 209.0 | 481.3 |
| 712 | 113.7 | 133.4 | 34.6 | 11.8 | 7.4 | 5.3 | 8.6 | 14.0 | 59.4 | 185.0 | 238.3 | 343.5 | 310.8 | 1030.8 | 1741.1 | 3462.7 |
| 758 | 97.0 | 118.7 | 32.5 | 10.2 | 3.1 | 10.0 | 35.1 | 74.0 | 203.9 | 415.0 | 594.3 | 692.9 | 670.0 | 1865.6 | 2763.5 | 4619.8 |
| 738 | 83.4 | 55.8 | 24.2 | 8.0 | 4.3 | 1.0 | 2.4 | CR | CR | 12.8 | 37.0 | 34.3 | 56.6 | 237.5 | 370.1 | 622.1 |
| 726 | 80.5 | 65.3 | 15.6 | 5.9 | 7.1 | 2.5 | 1.2 | CR | CR | CR | CR | CR | CR | CR | CR | CR |
| 716(nn) | 57.3 | 49.8 | 11.4 | 3.2 | 2.3 | CR | CR | 4.1 | 4.8 | 9.7 | 67.8 | 68.2 | 43.4 | 211.3 | 359.3 | 803.9 |
| 727 | 45.5 | 45.0 | 17.0 | 6.8 | 4.9 | 5.4 | CR | CR | 4.6 | 23.2 | 56.2 | 74.5 | 75.1 | 191.6 | 378.9 | 515.2 |
| mean | 104.2 | 129.8 | 51.7 | 25.6 | 13.2 | 7.3 | 11.0 | 26.9 | 65.7 | 126.3 | 199.8 | 225.9 | 204.0 | 601.9 | 944.7 | 1657.1 |
| se | 19.7 | 39.2 | 23.4 | 14.6 | 7.9 | 2.9 | 5.4 | 13.4 | 33.2 | 58.6 | 78.6 | 92.1 | 87.7 | 244.4 | 361.9 | 633.2 |

| EDO 60 # | Days from inoculum | | | | | | | | | |
|---|---|---|---|---|---|---|---|---|---|---|
| | 9 | 11 | 14 | 16 | 18 | 21 | 23 | 25 | 28 | 30 |
| 709 | 304.5 | 394.6 | 307.3 | 187.0 | 122.1 | 77.3 | 108.1 | 94.0 | 66.2 | 88.0 |
| 723 | 124.5 | 149.3 | 81.3 | 29.3 | 9.6 | 2.1 | 0.4 | 1.1 | CR | CR |
| 749 | 100.8 | 134.2 | 71.3 | 35.4 | 29.0 | 17.0 | 31.9 | 48.5 | 28.4 | 77.1 |
| 740 | 87.5 | 64.9 | 29.0 | 11.5 | 6.2 | 3.3 | 5.7 | 5.7 | 13.6 | 41.0 |
| 721 | 82.1 | 141.3 | 51.6 | 23.9 | 12.2 | 5.5 | 0.6 | CR | CR | CR |
| 735 | 70.7 | 60.8 | 20.5 | 10.7 | 3.4 | 3.6 | 2.1 | 9.0 | 3.3 | 8.9 |
| 713 | 52.7 | 70.8 | 32.0 | 8.6 | 7.9 | 3.3 | 3.3 | 3.2 | 2.9 | 3.7 |
| 729 | 26.2 | 26.9 | 16.1 | 7.5 | 3.4 | 0.7 | 0.6 | 1.3 | CR | CR |
| mean | 106.1 | 130.4 | 76.1 | 39.2 | 24.2 | 14.1 | 19.1 | 23.2 | 22.9 | 43.7 |
| se | 30.2 | 40.9 | 34.1 | 21.4 | 14.3 | 9.2 | 13.3 | 13.4 | 11.8 | 17.2 |

TABLE 1-continued

TC-71 tumour weight (mg) during the in vivo evaluation of EDO-S101 (treatments started on day 9).

| EDO 60 | Days from inoculum | | | | | | | |
|---|---|---|---|---|---|---|---|---|
| # | 32 | 35 | 38 | 42 | 45 | 49 | 53 | 56 |
| 709 | 195.4 | 295.9 | 345.1 | 562.9071 | 889.1 | 971.4 | 1459.1 | 2228.2 |
| 723 | CR | CR | CR | CR | CR | CR | CR | CR |
| 749 | 161.5 | 201.8 | 307.2 | 681.301 | 725.2 | 858.8 | 1050.5 | 2084.3 |
| 740 | 185.8 | 224.9 | 322.5 | 589.6573 | 1089.8 | 1414.8 | 2074.7 | 2978.8 |
| 721 | CR | CR | CR | CR | CR | CR | CR | CR |
| 735 | 37.0 | 41.1 | 44.6 | 113.6766 | 246.5 | 475.3 | 623.0 | 1546.2 |
| 713 | 17.2 | 11.6 | 10.0 | 35.99503 | 56.1 | 102.8 | 179.3 | 380.7 |
| 729 | CR | CR | CR | CR | CR | 29.0 | 50.8 | 76.2 |
| mean | 119.4 | 155.1 | 205.8 | 396.7 | 601.3 | 642.0 | 906.2 | 1549.1 |
| se | 38.2 | 55.0 | 73.4 | 133.4 | 194.9 | 219.6 | 317.9 | 459.2 |

| EDO 40 | Days from inoculum | | | | | | | | | | |
|---|---|---|---|---|---|---|---|---|---|---|---|
| # | 9 | 11 | 14 | 16 | 18 | 21 | 23 | 25 | 28 | 30 | 32 |
| 720 | 210.6 | 398.0 | 482.6 | 732.9 | 1028.4 | 1377.1 | 1901.8 | 1964.4 | 2668.1 | 3428.9 | 3598.6 |
| 739 | 147.7 | 222.8 | 244.5 | 274.3 | 437.5 | 312.3 | 377.8 | 473.5 | 420.1 | 513.3 | 650.1 |
| 701 (759) | 112.5 | 185.7 | 150.6 | 208.5 | 227.9 | 174.8 | 329.7 | 349.6 | 515.7 | 927.1 | 1375.3 |
| 730 | 110.5 | 145.9 | 130.2 | 127.4 | 176.0 | 194.1 | 273.0 | 257.3 | 405.6 | 763.7 | 1254.2 |
| 707 | 85.6 | 159.8 | 133.7 | 129.2 | 114.7 | 132.0 | 220.8 | 299.0 | 505.4 | 793.9 | 1384.8 |
| 745 | 72.3 | 110.1 | 93.9 | 151.1 | 225.3 | 217.6 | 458.2 | 456.3 | 570.1 | 827.6 | 1164.4 |
| 751 | 51.9 | FD | | | | | | | | | |
| 734 | 37.4 | 40.4 | 28.7 | 31.8 | 25.7 | 30.6 | 39.9 | 35.8 | 51.6 | 134.4 | 205.0 |
| mean | 103.5 | 180.4 | 180.6 | 236.4 | 319.3 | 348.4 | 514.5 | 548.0 | 733.8 | 1055.5 | 1376.1 |
| se | 19.8 | 42.4 | 56.0 | 87.5 | 127.5 | 174.5 | 236.6 | 242.4 | 328.8 | 408.2 | 405.3 |

| Irinotecan | Days from inoculum | | | | | | | | | | | | | | | | |
|---|---|---|---|---|---|---|---|---|---|---|---|---|---|---|---|---|---|
| TL,1 # | 9 | 11 | 14 | 16 | 18 | 21 | 23 | 25 | 28 | 30 | 32 | 35 | 38 | 42 | 45 | 49 | 53 |
| 746 | 316.8 | 273.1 | 87.8 | 99.6 | 44.2 | 9.6 | 13.2 | 9.9 | 6.8 | 15.4 | 83.7 | 223.4 | 713.8 | 2687.8 | 2443.2 | 2887.4 | 3331.8 |
| 731 | 124.6 | 90.6 | 16.6 | 41.5 | 11.3 | 2.4 | 1.7 | CR | CR | CR | CR | CR | CR | CR | CR | CR | CR |
| 753 | 103.5 | 45.7 | 9.9 | 23.8 | 8.8 | 6.1 | 5.4 | 3.3 | 1.5 | 2.7 | 8.2 | 42.7 | 105.6 | 327.2 | 627.6 | 1184.6 | 1062.6 |
| 708 | 88.1 | 63.3 | 17.1 | 72.8 | 28.1 | 7.5 | CR | CR | CR | CR | CR | CR | CR | CR | CR | CR | CR |
| 715 | 77.9 | 51.1 | 13.3 | 5.1 | 1.9 | CR | CR | CR | CR | CR | CR | CR | CR | CR | CR | CR | CR |
| 737 | 61.1 | 31.1 | 9.3 | 7.0 | 2.3 | 1.9 | 1.6 | CR | CR | CR | CR | CR | CR | CR | CR | CR | CR |
| 732 | 51.2 | 28.2 | 7.3 | 6.9 | 5.1 | 2.2 | 9.2 | 7.2 | 3.3 | 3.8 | 12.1 | 36.0 | 74.5 | 346.6 | 589.7 | 1244.3 | 2135.1 |
| 704 | 28.4 | 27.9 | 19.2 | 22.9 | 16.6 | 12.9 | 0.8 | 3.1 | 2.5 | 2.6 | 9.2 | 53.8 | 145.5 | 199.0 | 305.0 | 316.1 | 308.0 |
| mean | 106.4 | 76.4 | 22.6 | 35.0 | 14.8 | 6.1 | 7.0 | 5.9 | 3.5 | 6.1 | 28.3 | 88.9 | 259.8 | 890.2 | 991.4 | 1408.1 | 1709.4 |
| se | 31.9 | 29.1 | 9.4 | 12.2 | 5.2 | 1.6 | 0.6 | 1.7 | 1.2 | 3.1 | 18.5 | 45.0 | 152.0 | 600.1 | 489.3 | 536.8 | 658.0 |

FD: Found Dead
CR: Complete Response

TABLE 2

Antitumour activity of EDO-S101 against TC-71 Ewing's sarcoma xenograft: statistical analysis

| | Days from inoculum | | | |
|---|---|---|---|---|
| | 14 | 16 | 18 | 21 |
| Vehicles vs. EDO 80 | p < 0.05 | p < 0.0001 | p < 0.0001 | p < 0.0001 |
| Vehicles vs. EDO 60 | p < 0.05 | p < 0.0001 | p < 0.0001 | p < 0.0001 |
| Vehicles vs. EDO 40 | ns | p < 0.001 | p < 0.0001 | p < 0.0001 |
| Vehicles vs. Irinotecan | p < 0.01 | p < 0.0001 | p < 0.0001 | p < 0.0001 |

TABLE 3

Mouse body weight (g) during the in vivo evaluation of EDO-S101 in TC-71 Ewing's sarcoma xenograft (treatments started on day 9).

Vehicles

| # | \multicolumn{13}{c}{Days from tumour inoculum} |
|---|---|---|---|---|---|---|---|---|---|---|---|---|---|
|   | 9 | 10 | 11 | 14 | 16 | 18 | 21 | 9 | 11 | 14 | 16 | 18 | 21 | 49 |

| # | 9 | 10 | 11 | 14 | 16 | 18 | 21 |
|---|---|---|---|---|---|---|---|
| 744 | 28.3 | 25.1 | 24.4 | 24 | 23.3 | 24.1 | 25.7 |
| 702 | 24.3 | 22.8 | 22.6 | 19.4 | 19.7 | 22.2 | 22.6 |
| 741 | 29.8 | 24 | 23.5 | 23.5 | 24.2 | 24.8 | 26.5 |
| 756 | 28.3 | 24.8 | 24.7 | 25 | 25.1 | 26 | 26.4 |
| 711 | 25.3 | 26.8 | 26 | 25.8 | 24.8 | 27 | 27.4 |
| 754 | 27.9 | 24.4 | 24.4 | 23.2 | 24.4 | 26.1 | 26.3 |
| 719 | 28.3 | 28.6 | 27.9 | 23.8 | 26.9 | 28 | 29.6 |
| 705 | 28.1 | 25.5 | 24.3 | 22.7 | 22.9 | 23.5 | 25.2 |
| Mean | 27.5 | 25.3 | 24.8 | 22.5 | 23.9 | 25.2 | 26.2 |
| se | 0.6 | 0.6 | 0.6 | 0.5 | 0.7 | 0.7 | 0.7 |
| BWL % | 0.0 | −9.5 | −11.1 | −19.3 | −14.3 | −9.6 | −6.1 |

EDO 80

| # | 9 | 11 | 14 | 16 | 18 | 21 | 49 |
|---|---|---|---|---|---|---|---|
| 710 | 28.4 | 26.1 | 28.9 | 29.7 | 30.2 | 25.8 | 29.8 |
| 747 | 25.3 | 23.8 | 25.2 | 25.7 | 24.6 | 24.8 | 26 |
| 712 | 26.1 | 26.6 | 30.8 | 31.5 | 31.4 | 32 | 30 |
| 758 | 26.6 | 26.6 | 28.2 | 28.4 | 28.4 | 27.6 | 32.3 |
| 738 | 28.5 | 27.9 | 27.7 | 28.2 | 28.7 | 28.2 | 31 |
| 726 | 27.5 | 26.6 | 28.5 | 28.8 | 29.8 | 29.9 | 28.3 |
| 716(nn) | 32 | 30.1 | 32.6 | 30 | 30.1 | 30 | 34.1 |
| 727 | 28.7 | 25.2 | 29 | 25.7 | 28.8 | 29 | 29.9 |
| Mean | 27.9 | 25.2 | 27.9 | 28.5 | 29.0 | 28.4 | 30.2 |
| se | 0.7 | 0.6 | 0.8 | 0.7 | 0.7 | 0.8 | 0.9 |
| BWL % | 0.0 | −4.6 | 3.6 | 2.1 | 5.3 | 3.2 | 8.2 |

EDO 60

| # | 9 | 10 | 11 | 14 | 16 | 18 | 21 | 23 | 25 | 28 | 30 | 32 | 35 | 38 | 42 | 46 | 49 | 53 | 56 |
|---|---|---|---|---|---|---|---|---|---|---|---|---|---|---|---|---|---|---|---|
| 709 | 26.7 | 24.4 | 24.4 | 24 | 24.8 | 24.8 | 25 | 24.1 | 25 | 24.8 | 26.3 | 25.8 | 25.8 | 25.1 | 25.5 | 25.1 | 27 | 25.7 | 29.2 |
| 723 | 25.4 | 25.3 | 25.1 | 24.4 | 25.4 | 23.5 | 21.2 | 20.9 | 21.5 | 22.2 | 21.9 | 21 | 22.8 | 20.7 | 21.8 | 22.9 | 23.8 | | |
| 749 | 27.9 | 25.5 | 25.3 | 25 | 25.9 | 24.4 | 25.1 | 23.5 | 25 | 25.3 | 26.8 | 25.9 | 24.8 | 25.5 | 25.7 | 26.6 | 28 | 26.6 | |
| 740 | 27.6 | 25.7 | 25.5 | 25.8 | 27 | 26.2 | 26.6 | 25.7 | 26.8 | 27.4 | 27.4 | 25.7 | 27.4 | 26.9 | 27.5 | 27 | 30 | 29.6 | |
| 721 | 29.2 | 27.2 | 26.6 | 27.4 | 27.4 | 26.1 | 26 | 25.3 | 26.2 | 28.3 | 28.5 | 27.5 | 27.3 | 26 | 25.8 | 26.1 | 29.1 | | |
| 735 | 29.2 | 28.1 | 27.2 | 27.7 | 28.7 | 27.4 | 25.7 | 26.2 | 27.8 | 28.3 | 28.7 | 27.4 | 27.8 | 24.8 | 28.3 | 27 | 30 | 27 | 27.9 |
| 713 | 26.5 | 24.1 | 23.6 | 24.5 | 25 | 24.8 | 27.8 | 25.6 | 27.5 | 25.6 | 26.5 | 25.8 | 25.8 | 27.3 | 26 | 27 | 28.1 | 28.1 | |
| 729 | 28.1 | 24.8 | 24 | 24 | 25.2 | 24 | 24.8 | 24.3 | 25.6 | 24 | 25.3 | 23.8 | 24.4 | 25.7 | 25.7 | 25.7 | 30 | 26.1 | |
| Mean | 27.6 | 25.6 | 25.2 | 25.4 | 26.2 | 25.2 | 25.0 | 24.4 | 25.3 | 25.6 | 26.4 | 25.4 | 25.8 | 25.1 | 25.8 | 25.4 | 26.7 | 26.7 | 28.1 |
| se | 0.5 | 0.5 | 0.4 | 0.5 | 0.5 | 0.5 | 0.7 | 0.7 | 0.7 | 0.7 | 0.8 | 0.7 | 0.6 | 0.7 | 0.7 | 0.7 | 0.7 | 0.7 | 0.7 |
| BWL % | 0.0 | −7.0 | −8.6 | −8.1 | −5.1 | −8.8 | −9.8 | −11.7 | −8.3 | −7.3 | −4.2 | −8.0 | −6.6 | −8.9 | −6.5 | −8.1 | −3.1 | −3.1 | 2.0 |

TABLE 3-continued

Mouse body weight (g) during the in vivo evaluation of EDO-S101 in TC-71 Ewing's sarcoma xenograft (treatments started on day 9).

EDO 40

| # | Days from tumour inoculum | | | | | | | | | | | |
|---|---|---|---|---|---|---|---|---|---|---|---|---|
| | 9 | 10 | 11 | 14 | 16 | 18 | 21 | 23 | 25 | 28 | 30 | 32 |
| 720 | 29.7 | 28.7 | 29.3 | 29.6 | 31.5 | 30 | 30.4 | 31.7 | 30.9 | 33.8 | 35 | 36 |
| 739 | 26.4 | 25.4 | 25.7 | 26 | 26.3 | 25.3 | 24.7 | 25.3 | 24.2 | 25.5 | 25.7 | 26.8 |
| 701 (759) | 26.2 | 24.9 | 25.2 | 25.5 | 26.2 | 24.8 | 25.4 | 26.2 | 25.2 | 27 | 27.3 | 27.3 |
| 730 | 27.8 | 25.7 | 26.2 | 27 | 26.8 | 26.2 | 26.1 | 26.8 | 26.1 | 27 | 27.6 | 28.1 |
| 707 | 27.7 | 25.8 | 25.4 | 26.4 | 28.1 | 25.8 | 26.8 | 27.9 | 27.3 | 28.6 | 29.6 | 28.7 |
| 745 | 24.8 | 22.9 | 23.6 | 24.8 | 24.8 | 24.3 | 24 | 25 | 24.4 | 25.5 | 26.6 | 26.5 |
| 751 | 28.3 | FD | | | | | | | | | | |
| 734 | 25.4 | 25.7 | 26.2 | 26.6 | 26.8 | 26.5 | 26.1 | 27 | 25.7 | 26.3 | 27.4 | 27.2 |
| Mean | 27.0 | 25.7 | 25.9 | 26.6 | 27.2 | 26.1 | 26.2 | 27.1 | 26.3 | 27.7 | 28.5 | 28.7 |
| se | 0.6 | 0.6 | 0.6 | 0.5 | 0.8 | 0.7 | 0.7 | 0.8 | 0.8 | 1.0 | 1.1 | 1.2 |
| BWL % | 0.0 | -5.4 | -4.0 | -1.6 | 0.7 | -3.4 | -3.0 | 0.3 | -2.9 | 2.3 | 5.3 | 6.0 |

Irinotecan

| # | Days from tumour inoculum | | | | | | | | | | | | | | | | | |
|---|---|---|---|---|---|---|---|---|---|---|---|---|---|---|---|---|---|---|
| | 9 | 10 | 11 | 14 | 16 | 18 | 21 | 23 | 25 | 28 | 30 | 32 | 35 | 38 | 42 | 46 | 49 | 53 |
| 746 | 27.7 | 25.3 | 25.7 | 25.3 | 26.2 | 25.7 | 26.7 | 26.2 | 25.3 | 27.2 | 27 | 27 | 28.3 | 27.3 | 29.4 | 28.7 | 30.7 | 31.8 |
| 731 | 29.4 | 26.5 | 26.9 | 27.3 | 28.1 | 26.6 | 27.4 | 27 | 26.3 | 28.1 | 28.5 | 28.5 | 30.2 | 28.9 | 30.9 | 29.4 | 30.5 | 29.5 |
| 753 | 28.6 | 26.7 | 26.7 | 28 | 27.7 | 27.1 | 27.1 | 27 | 25.7 | 26.1 | 27 | 27.4 | 27.3 | 26.1 | 27.4 | 27.9 | 28.5 | 25 |
| 708 | 25.7 | 24 | 23.5 | 25.5 | 25.5 | 24.9 | 24.5 | 24.7 | 24.4 | 24.2 | 25.3 | 25.2 | 25.9 | 26.1 | 26.1 | 26.1 | 25.5 | 25.8 |
| 715 | 29.4 | 26.6 | 26 | 27.9 | 27.9 | 25.5 | 27 | 27.1 | 25.7 | 27 | 27.4 | 27.4 | 28.7 | 26.8 | 28.6 | 27.8 | 28.3 | 27.4 |
| 737 | 26.1 | 24.9 | 25.3 | 26.2 | 25.7 | 25.8 | 26 | 26.2 | 25 | 26.6 | 27 | 26.6 | 27.1 | 26.6 | 28 | 27.4 | 27.9 | 29 |
| 732 | 26 | 26 | 26.1 | 26.6 | 26.3 | 25.4 | 25.7 | 26.6 | 25.8 | 26.9 | 27 | 26.3 | 27.9 | 28.1 | 28.6 | 28 | 29.2 | 29.8 |
| 704 | 26.8 | 25.6 | 24.8 | 26.9 | 27.5 | 26.0 | 26.2 | 26.6 | 24.7 | 25.6 | 27.6 | 27.6 | 28.2 | 28 | 29.1 | 28.2 | 29.1 | 29.9 |
| Mean | 27.4 | 25.8 | 25.6 | 26.9 | 27.0 | 26.0 | 26.2 | 26.3 | 25.4 | 26.4 | 27.1 | 27.0 | 28.2 | 27.2 | 28.4 | 27.8 | 28.4 | 28.1 |
| se | 0.6 | 0.4 | 0.4 | 0.3 | 0.4 | 0.3 | 0.4 | 0.3 | 0.2 | 0.4 | 0.3 | 0.4 | 0.5 | 0.4 | 0.5 | 0.3 | 0.5 | 0.7 |
| BWL % | 0.0 | -6.1 | -6.6 | -1.9 | -1.7 | -5.3 | -4.3 | -3.5 | -7.5 | -3.9 | -1.1 | -1.6 | 1.7 | -0.7 | 3.5 | 1.5 | 3.6 | 2.3 |

FD: Found Dead
CR: Complete Response

Example 2

Antitumour Activity and Drug Tolerability in DD013 Dedifferentiated Sarcoma Model DD013 dedifferentiated liposarcoma were established and maintained in nude mice as described in Frapolli R. et al Clin Cancer Res 2010 16: 4958-4967. Briefly, xenografts were obtained by transplanting 3-4 mm tumour fragments s.c. in the flanks of mice. The growing tumour masses were measured with the aid of a Vernier caliper, and the tumour weights (TW, 1 mm$^3$=1 mg) were calculated by the formula: length×(width)$^2$/2. When tumour load achieved about 200-400 mg, mice were randomized into the experimental groups.

Figure 2:
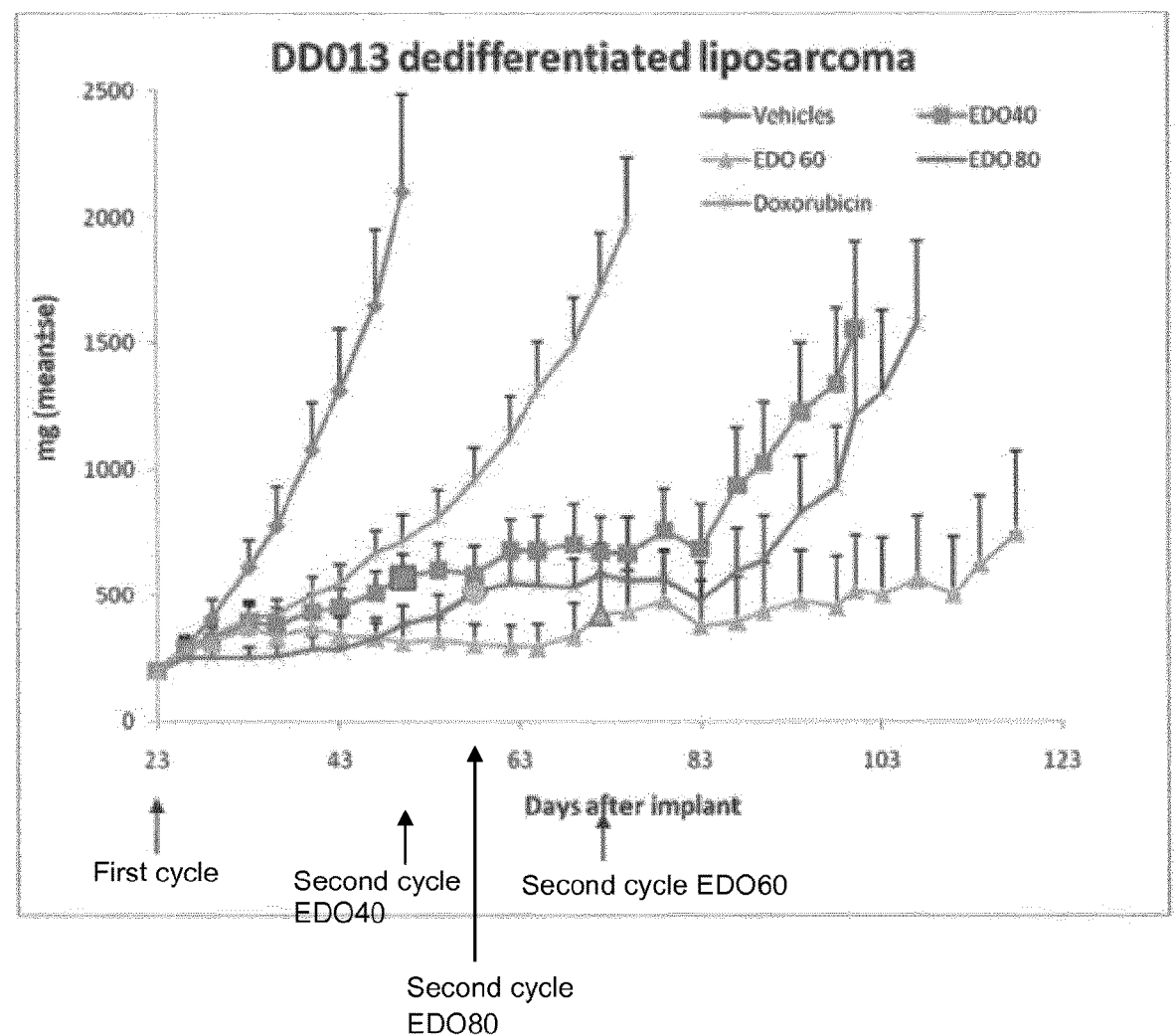
FIG. 2 shows the antitumoural activity of EDO-S101 against DD013 dedifferentiated liposarcoma sarcoma.

FIG. 2 shows the antitumour activity of EDO-S101 administered at different doses and schedules to DD013 bearing mice. The second cycles were administered when tumours started to regrow on day 50, 58 and 72 for EDO-S101 doses of 40, 80 and 60 mg/kg, respectively. Treatment of tumour-bearing mice with EDO-S101 (80 and 60 mg/kg) induced tumour growth arrest with an optimal T/C on day 50 of 18% and 14%, for 80 and 60 mg/kg respectively. Despite similar T/C values for these dose regimens, administration of 60 mg/kg q7dx3 resulted in a more sustained arrest of tumour growth, compared to administration of a single dose of 80 mg/kg. The administration of a second cycle of EDO-S101 (60 mg/kg) sustained tumour growth arrest, and significantly reduced tumour growth over a prolonged period towards the conclusion of the experiment. Tumour growth arrest was also observed following the administration of a second cycle in the group receiving 80 mg/kg of EDO-S101.

Mice treated with EDO-S101 (40 mg/kg) q7dx3 revealed reduced tumour growth, but without a complete arrest. Administration of the second cycle of treatment, however, promoted tumour growth arrest under this dose regimen. The optimal T/C was 27.2% on day 50.

Doxorubicin was used as positive control. Administration of 8 mg/kg of doxorubicin q7dx2 resulted in reduced tumour growth rate compared to the negative control, with an optimal T/C of 34.1%. No arrest of tumour growth was observed in mice treated with doxorubicin. Tumour weights for each animal and day are reported in table 4. The statistical analysis is reported in table 5.

BWL<5% was recorded at all doses and schedules. One mouse in the group treated with 80 mg/kg EDO-S101 was sacrificed due to a rapid BWL>30% occurring between day 75 and 79 from inoculum (about three weeks after the administration of the second cycle) of treatments.

Necropsy revealed no macroscopically detectable causes of death. Doxorubicin 8 mg/kg was well tolerated with a maximum BWL of 5.2% recorded on day 33. Table 6 reports the mouse body weights recorded throughout the experiment.

TABLE 4

DD0113 tumour weight (mg) during the in vivo evaluation of EDO-S101 (treatments started on day 23).

| Vehicles | Days from inoculum | | | | | | | | |
|---|---|---|---|---|---|---|---|---|---|
| # | 23 | 26 | 29 | 33 | 36 | 40 | 43 | 47 | 50 |
| 5 | 389.8 | 534.0 | 830.6 | 1138.4 | 1630.3 | 2043.6 | 2584.8 | 3155.1 | 3991.9 |
| 20 | 272.3 | 420.7 | 600.3 | 839.1 | 1043.5 | 1436.5 | 1723.4 | 2182.9 | 2403.8 |
| 34 | 246.5 | 353.8 | 551.5 | 670.0 | 931.2 | 1148.0 | 1417.8 | 1682.9 | 2114.3 |
| 69 | 224.6 | 208.9 | 272.4 | 458.5 | 524.2 | 775.6 | 948.2 | 1139.0 | 1593.6 |
| 17 | 187.0 | 358.8 | 471.1 | 813.2 | 1023.0 | 1489.2 | 1702.9 | 2394.3 | 3198.3 |
| 11 | 159.0 | 286.4 | 401.9 | 784.3 | 924.7 | 1346.0 | 1843.4 | 2206.4 | 2947.1 |
| 16 | 118.3 | 139.0 | 159.3 | 251.3 | 259.6 | 304.2 | 302.1 | 372.1 | 395.4 |
| 29 | 102.5 | 174.7 | 197.2 | 324.8 | 353.9 | 606.3 | 630.8 | 746.7 | 972.6 |
| 10 | 93.2 | 149.7 | 169.3 | 235.0 | 306.9 | 543.2 | 649.3 | 955.2 | 1279.3 |
| Mean | 199.2 | 291.8 | 406.0 | 612.7 | 777.4 | 1077.0 | 1311.4 | 1648.3 | 2099.6 |
| se | 31.9 | 45.3 | 76.5 | 104.1 | 150.8 | 186.5 | 244.1 | 302.9 | 385.5 |

| EDO40 | Days from inoculum | | | | | | | | | | | | | |
|---|---|---|---|---|---|---|---|---|---|---|---|---|---|---|
| # | 23 | 26 | 29 | 33 | 36 | 40 | 43 | 47 | 50 | 54 | 58 | 62 | 65 | 69 |
| 3 | 376.6 | 541.5 | 577.2 | 733.4 | 740.0 | 853.1 | 874.8 | 951.5 | 1015.8 | 1218.3 | 1198.4 | 1270.3 | 1227.3 | 1303.1 |
| 49 | 272.5 | 407.4 | 528.9 | 620.3 | 636.3 | 647.3 | 620.0 | 867.8 | 910.3 | 849.1 | 939.5 | 1057.1 | 1277.6 | 1503.3 |
| 46 | 234.4 | 341.7 | 304.2 | 386.0 | 313.7 | 394.8 | 382.2 | 374.0 | 477.7 | 407.8 | 361.1 | 400.9 | 371.1 | 405.2 |
| 43 | 224.8 | 312.6 | 326.8 | 398.8 | 375.3 | 445.1 | 452.6 | 447.7 | 675.3 | 650.3 | 647.5 | 778.6 | 690.9 | 866.7 |
| 36 | 191.1 | 284.8 | 350.2 | 400.6 | 376.9 | 470.3 | 614.9 | 502.6 | 556.8 | 641.5 | 526.9 | 706.2 | 485.1 | 447.9 |
| 35 | 172.9 | 244.9 | 315.8 | 410.8 | 408.8 | 402.2 | 419.5 | 504.6 | 593.9 | 566.8 | 517.8 | 694.4 | 740.8 | 712.6 |
| 44 | 124.8 | 208.4 | 218.0 | 307.5 | 294.7 | 363.7 | 359.8 | 551.2 | 509.8 | 653.1 | 678.7 | 795.3 | 906.7 | 742.0 |
| 58 | 103.7 | 138.3 | 150.5 | 165.2 | 125.0 | 150.4 | 143.6 | 155.1 | 166.1 | 138.4 | 148.4 | 127.1 | 153.2 | 124.4 |
| 54 | 86.8 | 72.8 | 101.4 | 127.5 | 151.8 | 174.0 | 194.8 | 211.9 | 228.8 | 270.3 | 238.9 | 271.1 | 247.5 | 223.2 |
| Mean | 198.6 | 283.6 | 319.2 | 394.4 | 380.3 | 433.4 | 451.3 | 507.4 | 570.5 | 599.5 | 584.1 | 677.9 | 677.8 | 703.2 |
| se | 30.5 | 47.0 | 52.4 | 64.3 | 67.2 | 72.5 | 75.4 | 88.3 | 92.6 | 106.1 | 110.7 | 121.6 | 134.9 | 155.8 |

| EDO40 | Days from inoculum | | | | | | | |
|---|---|---|---|---|---|---|---|---|
| # | 72 | 75 | 79 | 83 | 87 | 90 | 94 | 98 | 100 |
| 3 | 1437.5 | 1469.1 | 1640.1 | 1758.9 | 2103.7 | 2135.1 | 2516.4 | 2716.0 | 3162.4 |
| 49 | 1078.7 | 1076.6 | 1320.3 | 1083.6 | 1649.4 | 1918.5 | 2036.1 | 1993.4 | 2274.9 |
| 46 | 409.0 | 425.4 | 560.8 | 394.8 | 526.5 | 598.6 | 820.3 | 913.4 | 963.9 |
| 43 | 909.6 | 836.1 | 876.4 | 1023.8 | 1294.1 | 1450.6 | 1686.1 | 1775.6 | 2276.4 |
| 36 | 438.2 | 429.0 | 387.3 | 391.4 | 457.1 | 463.8 | 542.4 | 446.5 | 533.5 |
| 35 | 702.4 | 742.0 | 854.9 | 677.5 | 994.3 | 1104.6 | 1322.5 | 1827.2 | 2007.9 |

TABLE 4-continued

DD0113 tumour weight (mg) during the in vivo evaluation of EDO-S101 (treatments started on day 23).

| | | | | | | | | |
|---|---|---|---|---|---|---|---|---|
| 44 | 638.6 | 670.3 | 755.9 | 567.8 | 1055.8 | 1165.7 | 1662.8 | 1853.1 | 2178.4 |
| 58 | 146.3 | 117.4 | 144.0 | 83.9 | 95.8 | 119.3 | 133.6 | 145.4 | 160.4 |
| 54 | 267.4 | 229.4 | 271.2 | 173.5 | 245.9 | 249.5 | 318.3 | 371.6 | 419.7 |
| Mean | 669.8 | 666.1 | 756.8 | 683.9 | 935.9 | 1022.8 | 1226.5 | 1338.0 | 1553.1 |
| se | 138.1 | 142.1 | 162.8 | 176.2 | 223.5 | 240.3 | 273.4 | 297.1 | 350.5 |

| ED60 | Days from inoculum | | | | | | | | | | | | | | |
|---|---|---|---|---|---|---|---|---|---|---|---|---|---|---|---|
| # | 23 | 26 | 29 | 33 | 36 | 40 | 43 | 47 | 50 | 54 | 58 | 62 | 65 | 69 | 72 | 75 |
| 39 | 390.7 | 581.5 | 713.8 | 959.2 | 752.3 | 858.2 | 788.1 | 784.4 | 753.8 | 868.2 | 862.4 | 887.6 | 998.1 | 1344.4 | 1654.5 | 1698.0 |
| 23 | 270.8 | 439.5 | 542.7 | 709.9 | 694.9 | 638.0 | 594.1 | 617.7 | 533.9 | 564.0 | 420.0 | 395.4 | 352.1 | 347.7 | 414.7 | 457.6 |
| 7 | 256.0 | 349.4 | 408.5 | 434.0 | 374.9 | 442.3 | 396.4 | 372.6 | 327.6 | 225.0 | 265.4 | 217.1 | 125.3 | 142.7 | 188.6 | 170.8 |
| 40 | 208.0 | 277.6 | 245.2 | 230.8 | 195.0 | 178.1 | 196.5 | 162.6 | 176.0 | 134.2 | 150.8 | 153.4 | 133.1 | 96.1 | 130.6 | 110.6 |
| 53 | 186.9 | 282.9 | 337.8 | 388.5 | 320.6 | 462.9 | 359.1 | 384.0 | 334.2 | 413.0 | 404.6 | 418.0 | 350.2 | 371.1 | 509.4 | 516.6 |
| 42 | 149.8 | 149.7 | 127.5 | 156.7 | 151.2 | 195.4 | 165.1 | 150.5 | 138.1 | 123.8 | 134.5 | 111.0 | 133.4 | 86.2 | 157.5 | 123.5 |
| 68 | 137.4 | 162.1 | 180.6 | 179.5 | 215.2 | 211.0 | 214.6 | 209.0 | 199.7 | 227.1 | 187.9 | 183.0 | 187.4 | 191.3 | 268.5 | 307.7 |
| 52 | 98.0 | 93.0 | 129.5 | 185.1 | 208.1 | 215.3 | 247.2 | 194.4 | 257.7 | 253.8 | 247.8 | 255.2 | 278.4 | 367.8 | 403.5 | 441.0 |
| 51 | 95.4 | 117.1 | 107.7 | 114.7 | 95.8 | 139.7 | 94.4 | 96.9 | 77.1 | 80.6 | 56.8 | 63.9 | 66.8 | 63.8 | 86.1 | 70.2 |
| Mean | 199.2 | 272.5 | 310.4 | 373.1 | 334.2 | 371.2 | 339.5 | 330.2 | 310.9 | 321.1 | 303.3 | 298.3 | 291.6 | 334.6 | 423.7 | 432.9 |
| se | 31.7 | 54.4 | 70.3 | 96.3 | 78.7 | 82.8 | 75.0 | 78.3 | 71.2 | 85.1 | 80.5 | 83.6 | 94.7 | 132.9 | 161.3 | 167.6 |

| ED60 | Days from inoculum | | | | | | | | | | | |
|---|---|---|---|---|---|---|---|---|---|---|---|---|
| # | 79 | 83 | 87 | 90 | 94 | 98 | 100 | 103 | 107 | 111 | 114 | 118 |
| 39 | 1977.8 | 1774.9 | 1753.1 | 1903.1 | 1967.5 | 1939.1 | 2099.8 | 2142.4 | 2405.7 | 2171.7 | 2520.5 | 3030.9 |
| 23 | 571.8 | 335.3 | 396.9 | 365.0 | 403.0 | 387.0 | 463.0 | 430.4 | 428.9 | 368.4 | 487.7 | 526.7 |
| 7 | 172.6 | 86.5 | 125.1 | 118.4 | 135.6 | 113.6 | 122.1 | 106.7 | 166.5 | 90.0 | 131.7 | 157.8 |
| 40 | 132.6 | 56.8 | 78.1 | 56.3 | 73.5 | 57.9 | 86.5 | 70.5 | 65.8 | 45.6 | 81.4 | 79.8 |
| 53 | 555.7 | 415.0 | 442.6 | 626.5 | 693.0 | 655.0 | 751.1 | 747.9 | 824.2 | 813.6 | 999.4 | 1342.5 |
| 42 | 152.1 | 71.0 | 82.4 | 82.7 | 95.1 | 70.1 | 87.0 | 89.6 | 103.8 | 62.2 | 119.1 | 134.3 |
| 68 | 256.1 | 193.9 | 209.1 | 234.7 | 279.8 | 225.1 | 297.7 | 231.0 | 255.2 | 245.9 | 284.3 | 364.6 |
| 52 | 404.7 | 426.4 | 423.2 | 492.6 | 598.8 | 584.9 | 718.0 | 670.9 | 777.9 | 686.9 | 935.9 | 1024.5 |
| 51 | 58.1 | 32.7 | 31.4 | 49.6 | 43.4 | 30.7 | 40.7 | 37.5 | 33.0 | 33.9 | 61.0 | 64.1 |
| Mean | 475.7 | 376.9 | 393.6 | 436.6 | 476.6 | 451.5 | 518.4 | 503.0 | 562.3 | 502.0 | 624.6 | 747.2 |
| se | 197.7 | 182.3 | 178.2 | 195.7 | 202.1 | 201.4 | 217.4 | 223.2 | 250.5 | 229.5 | 265.6 | 322.2 |

| EDO80 | Days from inoculum | | | | | | | | | | | | | | |
|---|---|---|---|---|---|---|---|---|---|---|---|---|---|---|---|
| # | 23 | 26 | 29 | 33 | 36 | 40 | 43 | 47 | 50 | 54 | 58 | 62 | 65 | 69 | 72 | 75 |
| 33 | 361.8 | 410.2 | 399.5 | 456.2 | 466.8 | 569.1 | 500.6 | 626.2 | 686.0 | 708.8 | 920.2 | 943.1 | 1025.7 | 1144.1 | 1339.2 | 1250.1 |
| 56 | 272.9 | 433.7 | 447.9 | 408.9 | 431.6 | 476.1 | 547.3 | 643.5 | 717.6 | 836.1 | 863.6 | 970.6 | 939.0 | 909.3 | 893.1 | 779.7 |
| 32 | 241.0 | 275.2 | 310.3 | 293.6 | 284.2 | 364.0 | 355.5 | 338.2 | 447.7 | 469.2 | 593.4 | 633.0 | 636.4 | 591.5 | 629.6 | 675.2 |
| 60 | 225.2 | 338.5 | 335.3 | 271.4 | 280.3 | 279.7 | 255.8 | 321.9 | 447.8 | 456.3 | 628.6 | 680.2 | 670.6 | 550.9 | 619.0 | 634.0 |
| 59 | 191.6 | 196.8 | 179.1 | 220.9 | 194.9 | 216.2 | 227.9 | 275.0 | 297.1 | 339.2 | 525.3 | 527.0 | 491.0 | 478.8 | 542.0 | 567.6 |
| 14 | 176.4 | 236.0 | 229.9 | 247.0 | 242.1 | 257.3 | 284.6 | 335.7 | 416.1 | 434.6 | 442.9 | 533.6 | 567.8 | 587.8 | 621.4 | 519.9 |
| 50 | 118.7 | 145.4 | 182.9 | 151.7 | 168.5 | 140.9 | 164.8 | 167.6 | 184.9 | 213.4 | 248.6 | 199.0 | 201.7 | 164.5 | 206.7 | 185.4 |
| 37 | 113.3 | 152.8 | 95.7 | 103.9 | 129.4 | 130.0 | 116.9 | 97.1 | 91.6 | 125.8 | 167.1 | 187.7 | 107.7 | 146.5 | 134.1 | 158.8 |
| 38 | 81.5 | 89.0 | 80.4 | 105.2 | 109.8 | 119.3 | 109.5 | 132.0 | 171.9 | 186.3 | 212.9 | 219.1 | 222.7 | 211.1 | 248.6 | 277.5 |
| Mean | 198.0 | 253.1 | 251.2 | 251.0 | 256.4 | 283.7 | 284.8 | 326.3 | 384.4 | 418.9 | 511.4 | 549.2 | 540.3 | 531.6 | 581.5 | 560.9 |
| se | 29.5 | 40.3 | 43.3 | 41.3 | 41.8 | 52.9 | 52.4 | 65.5 | 73.5 | 79.1 | 90.8 | 100.1 | 107.1 | 112.6 | 125.3 | 113.4 |

| EDO80 | Days from inoculum | | | | | | | | |
|---|---|---|---|---|---|---|---|---|---|
| # | 79 | 83 | 87 | 90 | 94 | 98 | 100 | 103 | 107 |
| 33 | 1330.0 | 1450.9 | 1616.4 | 1617.7 | 2114.0 | 2225.7 | 3065.0 | 2981.4 | 3037.4 |
| 56 | 618.2 | | | | | | | | |
| 32 | 650.1 | 575.5 | 647.4 | 735.1 | 1048.7 | 1385.7 | 1722.4 | 1979.3 | 2529.3 |
| 60 | 690.9 | 509.7 | 823.3 | 987.9 | 1242.6 | 1194.7 | 1733.1 | 1845.5 | 2157.8 |
| 59 | 573.1 | 400.2 | 496.0 | 466.5 | 555.8 | 782.4 | 996.2 | 1231.1 | 1395.6 |
| 14 | 621.4 | 507.9 | 665.8 | 740.1 | 814.4 | 918.1 | 1052.7 | 1125.6 | 1619.3 |
| 50 | 212.9 | 115.7 | 136.4 | 153.4 | 240.1 | 164.4 | 303.2 | 320.3 | 476.4 |
| 37 | 135.0 | 117.9 | 195.7 | 227.0 | 306.5 | 464.1 | 413.3 | 529.9 | 745.4 |
| 38 | 245.2 | 122.5 | 171.6 | 182.9 | 285.8 | 282.5 | 392.7 | 396.4 | 619.0 |
| Mean | 564.1 | 475.0 | 594.1 | 638.8 | 826.0 | 927.2 | 1209.8 | 1301.2 | 1572.5 |
| se | 119.3 | 155.3 | 172.3 | 176.4 | 226.0 | 239.1 | 332.0 | 327.1 | 333.6 |

| Doxorubicin | Days from inoculum | | | | | | | | | | | | | | |
|---|---|---|---|---|---|---|---|---|---|---|---|---|---|---|---|
| # | 23 | 26 | 29 | 33 | 36 | 40 | 43 | 47 | 50 | 54 | 58 | 62 | 65 | 69 | 72 | 75 |
| 25 | | 302.2 | 464.9 | 492.1 | 566.5 | 549.6 | 578.4 | 529.7 | 623.2 | 561.6 | 776.9 | 819.5 | 955.7 | 960.1 | 1238.0 | 1440.5 | 1747.2 |
| 57 | | 277.0 | 410.3 | 380.4 | 526.0 | 572.5 | 652.6 | 810.5 | 800.6 | 1087.6 | 1060.5 | 1324.9 | 1686.9 | 1836.1 | 2045.0 | 2313.3 | 2786.0 |
| 65 | | 253.6 | 365.9 | 478.9 | 691.7 | 610.4 | 762.1 | 868.0 | 1056.8 | 1194.0 | 1306.3 | 1508.4 | 1777.9 | 2144.7 | 2383.0 | 2810.6 | 3155.1 |
| 61 | | 228.6 | 384.0 | 477.1 | 549.2 | 519.4 | 750.9 | 780.2 | 1025.8 | 996.7 | 1175.7 | 1392.3 | 1604.2 | 1949.8 | 2019.6 | 2245.9 | 2700.8 |

TABLE 4-continued

DD0113 tumour weight (mg) during the in vivo evaluation of EDO-S101 (treatments started on day 23).

| | | | | | | | | | | | | | | | |
|---|---|---|---|---|---|---|---|---|---|---|---|---|---|---|---|
| 12 | 196.0 | 308.8 | 398.0 | 444.0 | 503.4 | 531.1 | 575.9 | 669.1 | 680.6 | 807.3 | 998.2 | 1087.3 | 1415.2 | 1526.2 | 1770.1 | 2034.9 |
| 21 | 178.0 | 283.4 | 313.2 | 344.6 | 361.9 | 424.1 | 420.0 | 636.6 | 642.9 | 620.9 | 733.0 | 777.9 | 837.9 | 909.3 | 1114.8 | 1086.0 |
| 62 | 147.0 | 232.9 | 252.9 | 295.0 | 345.6 | 401.6 | 428.4 | 529.5 | 583.1 | 693.3 | 855.0 | 1128.3 | 1390.9 | 1605.4 | 1904.1 | 2058.0 |
| 8 | 114.2 | 124.9 | 147.9 | 150.3 | 240.6 | 244.9 | 263.0 | 430.2 | 405.8 | 465.0 | 563.7 | 667.3 | 744.7 | 834.8 | 903.5 | 1112.1 |
| 64 | 97.6 | 87.4 | 89.3 | 115.0 | 128.9 | 151.8 | 212.3 | 224.5 | 292.0 | 387.3 | 428.2 | 471.1 | 532.1 | 860.3 | 908.8 | 1057.2 |
| Mean | 199.3 | 295.8 | 336.6 | 409.1 | 425.8 | 499.7 | 543.1 | 666.3 | 716.0 | 810.3 | 958.1 | 1128.5 | 1312.4 | 1491.3 | 1712.4 | 1970.8 |
| se | 23.9 | 42.7 | 49.2 | 65.6 | 55.1 | 71.1 | 79.1 | 89.1 | 103.4 | 104.8 | 126.1 | 156.3 | 192.6 | 191.0 | 224.3 | 264.0 |

† sacrificed moribund

TABLE 5

Antitumour activity of EDO-S101 against DD013 dedifferentiated liposarcoma xenograft: statistical analysis

| | Days from inoculum | | | | |
|---|---|---|---|---|---|
| | 36 | 40 | 43 | 47 | 50 |
| Vehicles vs. EDO 80 | $p < 0.05$ | $p < 0.0001$ | $p < 0.0001$ | $p < 0.0001$ | $p < 0.0001$ |
| Vehicles vs. EDO 60 | $p < 0.01$ | $p < 0.0001$ | $p < 0.0001$ | $p < 0.0001$ | $p < 0.0001$ |
| Vehicles vs. EDO 40 | ns | $p < 0.001$ | $p < 0.0001$ | $p < 0.0001$ | $p < 0.0001$ |
| Vehicles vs. Doxorubicin | ns | $p < 0.01$ | $p < 0.0001$ | $p < 0.0001$ | $p < 0.0001$ |

TABLE 6

Mouse body weight (g) during the in vivo evaluation of EDO-S101 in DD013 dedifferentiated liposarcoma xenograft (treatments started on day 23).

Vehicles

| # | Days from inoculum | | | | | | | | | |
|---|---|---|---|---|---|---|---|---|---|---|
| | 23 | 26 | 29 | 33 | 36 | 40 | 43 | 47 | 50 | |
| 5 | 22.9 | 22.7 | 23.3 | 24.2 | 25.6 | 25.7 | 26.1 | 26.6 | 27.7 | |
| 20 | 26 | 27.2 | 27.4 | 27.3 | 28.3 | 30.1 | 29.6 | 30 | 30.5 | |
| 34 | 21.8 | 21.4 | 22.1 | 22.7 | 23.5 | 24.6 | 24.1 | 25.3 | 24.7 | |
| 69 | 24.1 | 25.3 | 25.3 | 25.6 | 26.3 | 26.2 | 26.7 | 27.4 | 28.2 | |
| 17 | 20 | 20.3 | 22.9 | 21.5 | 22.3 | 22.4 | 22.6 | 23.6 | 25.4 | |
| 11 | 25.3 | 25.8 | 27.1 | 27.5 | 28.1 | 28.7 | 29.2 | 29.2 | 30.6 | |
| 16 | 21.6 | 22.2 | 23.2 | 23 | 23.7 | 23.7 | 24 | 24.1 | 25.2 | |
| 29 | 21.4 | 22.7 | 22.2 | 23.3 | 23.5 | 24.2 | 23.8 | 23.9 | 24.4 | |
| 10 | 23 | 23.6 | 27.4 | 24.4 | 24.8 | 25.3 | 25 | 25.3 | 25 | |
| Mean | 22.9 | 23.5 | 24.7 | 24.5 | 25.1 | 25.7 | 25.7 | 26.2 | 26.9 | |
| se | 0.6 | 0.7 | 0.6 | 0.7 | 0.7 | 0.8 | 0.8 | 0.8 | 0.8 | |
| BWL % | 0.0 | 2.5 | 4.6 | 6.5 | 9.7 | 12.0 | 12.1 | 14.2 | 17.3 | |

EDO40

| # | Days from inoculum | | | | | | | | | | | | | | |
|---|---|---|---|---|---|---|---|---|---|---|---|---|---|---|---|
| | 23 | 26 | 29 | 33 | 36 | 40 | 43 | 47 | 50 | 54 | 58 | 62 | 65 | 69 | 72 | 75 |
| 3 | 23.3 | 22.7 | 23.3 | 23.5 | 24.1 | 24.3 | 24.4 | 26 | 26.1 | 26 | 25.8 | 25.6 | 25.9 | 26.7 | 27 | 27 |
| 49 | 24.8 | 24.6 | 26 | 25.3 | 25.7 | 26.9 | 26.5 | 27 | 27.5 | 27.2 | 27.2 | 27.7 | 25.9 | 28.9 | 28.9 | 29.3 |
| 46 | 23.5 | 23.4 | 24.8 | 23.4 | 24.6 | 25.2 | 24.9 | 26.1 | 26.1 | 25.3 | 25.2 | 27 | 25.7 | 26 | 26.5 | 27.1 |
| 43 | 25.5 | 23.1 | 25.3 | 24.5 | 25.3 | 25.8 | 25.7 | 26.9 | 26.4 | 26.4 | 25.3 | 23.8 | 25 | 27.3 | 26.3 | 27.9 |
| 36 | 21.7 | 21.8 | 22.9 | 22.9 | 22.7 | 22.8 | 23.5 | 24 | 24.4 | 29 | 23.4 | 25.2 | 23.3 | 25.3 | 24.8 | 24.9 |
| 35 | 26 | 25.5 | 27.1 | 26.6 | 26.9 | 28.2 | 27.9 | 28.7 | 28.7 | 24.6 | 28.7 | 26 | 29.6 | 30 | 30.3 | 30.6 |
| 44 | 21.6 | 20.8 | 23.2 | 22.8 | 23.3 | 23.2 | 23.2 | 25 | 25.2 | 22.1 | 24.3 | 21.8 | 24.5 | 25 | 25.6 | 26 |
| 58 | 21.1 | 21 | 22.2 | 21.3 | 21.6 | 21.6 | 21.8 | 22.4 | 23.4 | 28.7 | 21.9 | 21.8 | 21.7 | 22.4 | 23.1 | 23.5 |
| 54 | 25 | 25.9 | 27.4 | 27.2 | 27.1 | 27.4 | 27.8 | 28.3 | 29.6 | 26 | 28.4 | 29.2 | 28.3 | 29.2 | 28.3 | 29.3 |
| Mean | 23.6 | 23.2 | 24.7 | 24.2 | 24.6 | 25 | 25.1 | 26 | 26.4 | 0.7 | 25.6 | 26.2 | 25.8 | 26.8 | 26.8 | 27.3 |
| se | 0.6 | 0.6 | 0.6 | 0.6 | 0.6 | 0.7 | 0.7 | 0.7 | 0.7 | 10.1 | 0.8 | 0.8 | 0.8 | 0.8 | 0.7 | 0.8 |
| BWL % | 0.0 | -1.7 | 4.6 | 2.4 | 4.1 | 6.1 | 6.2 | 10.3 | 11.7 | | 8.3 | 11.0 | 9.1 | 13.3 | 13.3 | 15.6 |

EDO 60

| # | Days from inoculum | | | | | | | | | | | | | | | | | | | | | |
|---|---|---|---|---|---|---|---|---|---|---|---|---|---|---|---|---|---|---|---|---|---|---|
| | 23 | 26 | 29 | 33 | 36 | 40 | 43 | 47 | 50 | 54 | 58 | 62 | 65 | 69 | 72 | 75 | 79 | 83 | 87 | 90 | 94 | 98 | 100 |
| 39 | 22.1 | 22.1 | 23.3 | 22.8 | 22.2 | 22.2 | 22.7 | 24.1 | 24.4 | 25.5 | 24.5 | 24.4 | 25.1 | 26 | 27.1 | 25.7 | 25 | 25.6 | 26.5 | 25.1 | 25.6 | 27.2 | 26.5 |
| 23 | 22.5 | 21.2 | 22.6 | 22.9 | 21.7 | 21.7 | 22.6 | 23.9 | 24.2 | 23.8 | 24.1 | 23.8 | 23.5 | 24.1 | 24.4 | 25.1 | 23 | 23.6 | 25.3 | 25.8 | 25.6 | 25.3 | 25.3 |
| 7 | 24 | 23.1 | 24.6 | 24.8 | 24.8 | 24.8 | 24.9 | 26.5 | 27 | 27.4 | 26.5 | 28.2 | 27.4 | 26.5 | 28.2 | 26.1 | 25.9 | 25.4 | 26.9 | 26 | 26 | 28.1 | 27.1 |
| 40 | 22.8 | 21.7 | 22.5 | 23.2 | 22.5 | 22.5 | 23.5 | 24.2 | 24.4 | 25.5 | 24.8 | 25.2 | 25.8 | 24.6 | 25.8 | 25.5 | 24.6 | 23.8 | 24.3 | 26.4 | 23.8 | 26.2 | 26.3 |
| 53 | 23.2 | 22.6 | 23.6 | 24 | 23.8 | 23.8 | 24.4 | 25.3 | 25.6 | 26.5 | 25.6 | 26 | 26.6 | 25.4 | 26.4 | 26.1 | 25.4 | 26.1 | 25.9 | 27.2 | 26.4 | 26.6 | 26.3 |
| 42 | 22.9 | 21.7 | 23.4 | 23 | 23 | 23.1 | 23.1 | 24.4 | 24.7 | 24.4 | 24.8 | 24.7 | 24.8 | 24.1 | 25.6 | 25.7 | 24.1 | 23.7 | 24.8 | 25 | 27.2 | 25.1 | 24.4 |
| 68 | 23.8 | 23 | 24.8 | 25.2 | 24.4 | 24.4 | 25.7 | 25.2 | 25.8 | 25.7 | 26.7 | 25.8 | 25.7 | 25.9 | 26.1 | 27.1 | 23.8 | 25.6 | 25 | 23.6 | 26.2 | 25.8 | 27.3 |

TABLE 6-continued

Mouse body weight (g) during the in vivo evaluation of EDO-S101 in DD013 dedifferentiated liposarcoma xenograft (treatments started on day 23).

Days from inoculum

| # | 23 | 26 | 29 | 33 | 36 | 40 | 43 | 47 | 50 | 54 | 58 | 62 | 65 | 69 | 72 | 75 | 79 | 83 | 87 | 90 | 94 | 98 | 100 | 103 | 107 |
|---|---|---|---|---|---|---|---|---|---|---|---|---|---|---|---|---|---|---|---|---|---|---|---|---|---|
| 52 | 25.3 | 24.9 | 24.6 | 25.9 | 25.3 | 26.1 | 27.1 | 27.4 | 27.6 | 27.7 | 27.2 | 26.9 | 26.8 | 26 | 26.1 | 26.9 | 25.5 | 28.6 | 28.5 | 28.9 | 29 | 28.1 | 28.8 | 28 | 29.5 |
| 51 | 23 | 23.8 | 22.3 | 23.4 | 22.5 | 23.1 | 23.8 | 24.8 | 25.3 | 25.1 | 26.5 | 26.2 | 24.5 | 23.2 | 21 | 20.7 | 16.6 | — | 21.7 | 23.2 | 22.5 | 22.1 | 22.8 | 21.7 | 20.8 |
| Mean | 23.3 | 23.7 | 23.1 | 23.9 | 23.2 | 24.1 | 25.2 | 25.4 | 25.5 | 25.5 | 25.9 | 26.3 | 24.8 | 24.8 | 24.5 | 24.6 | 24.8 | — | 25.3 | 25.7 | 25.7 | 25.7 | 25.6 | 25.3 | 25.5 |
| se | 0.3 | 0.3 | 0.4 | 0.4 | 0.5 | 0.5 | 0.4 | 0.4 | 0.4 | 0.4 | 0.3 | 0.3 | 0.4 | 0.6 | 0.6 | 0.6 | 0.6 | — | 0.7 | 0.6 | 0.6 | 0.6 | 0.6 | 0.8 | 0.9 |
| BWL % | 0.0 | 1.7 | −0.8 | 2.5 | −0.6 | 8.0 | 8.3 | 9.6 | 9.5 | 10.2 | 10.2 | 11.0 | 12.7 | 11.6 | 6.2 | 5.2 | 5.5 | 6.4 | 8.2 | 10.1 | 10.2 | 10.3 | 9.6 | 8.5 | 9.1 |

EDO 80

Days from inoculum

| # | 23 | 26 | 29 | 33 | 36 | 40 | 43 | 47 | 50 | 54 | 58 | 62 | 65 | 69 | 72 | 75 | 79 | 83 | 87 | 90 | 94 | 98 | 100 | 103 | 107 |
|---|---|---|---|---|---|---|---|---|---|---|---|---|---|---|---|---|---|---|---|---|---|---|---|---|---|
| 33 | 26.1 | 23.4 | 22.7 | 25.1 | 28.3 | 28.6 | 28.5 | 28.4 | 27.9 | 27.7 | 28.7 | 25.7 | 27.2 | 28.7 | 30.7 | 30.6 | 28.7 | 24.1 | 25.3 | 29.2 | 31 | 31.1 | 29.7 | 25.9 | 26 |
| 56 | 25.7 | 23.6 | 22.6 | 25.1 | 27 | 27.2 | 26.5 | 27.9 | 28.3 | 28.4 | 29.8 | 24.4 | 24.1 | 25.1 | 23.1 | 21.8 | 16.6 | † | | | | | | | |
| 32 | 25 | 22 | 21.5 | 24 | 25.3 | 27 | 26 | 26.1 | 26.8 | 26.7 | 28 | 23.9 | 24.7 | 25.8 | 27.5 | 27.4 | 26.2 | 21.1 | 23.9 | 28 | 29.1 | 29.9 | 28.6 | 28.3 | 23.3 |
| 60 | 23.1 | 21.3 | 22.2 | 23.3 | 25.6 | 25.7 | 25 | 25.4 | 25.4 | 25.8 | 28 | 24 | 25.2 | 26 | 26.5 | 26.3 | 26.3 | 26.8 | 27.2 | 28.2 | 28.9 | 28 | 27.6 | 28.4 | 28.4 |
| 59 | 24 | 20.9 | 21 | 23.1 | 24.7 | 26 | 25.6 | 24.6 | 24.6 | 25 | 26.9 | 22.7 | 23.1 | 24.4 | 26.5 | 27.4 | 24.6 | 25 | 20.4 | 18.3 | 23.3 | 27.6 | 27.3 | 26.7 | 24.5 |
| 14 | 23.3 | 20.1 | 21 | 21.9 | 23.8 | 24.4 | 25 | 24.2 | 24.4 | 24.5 | 25 | 21.9 | 22.8 | 24.1 | 25.2 | 27.2 | 24.1 | 26.3 | 24.8 | 26.1 | 25.9 | 26.1 | 26.1 | 27.1 | 25.4 |
| 50 | 26.2 | 22.4 | 21.6 | 24.9 | 26.3 | 27.9 | 26.9 | 27.4 | 26.3 | 28 | 27.6 | 23.7 | 24.1 | 26.4 | 25.5 | 27.6 | 27.6 | 26.3 | 27.1 | 24.4 | 28.5 | 28.6 | 28.1 | 28.2 | 27.5 |
| 37 | 22.4 | 21.6 | 21.6 | 22.5 | 24.2 | 24 | 24.2 | 27.4 | 23.2 | 24.8 | 24.9 | 23.8 | 23.1 | 23.9 | 25 | 27.4 | 26 | 25.3 | 24.2 | 26 | 26 | 24.6 | 25.1 | 25.4 | 26.4 |
| 38 | 22.3 | 21.9 | 21 | 23.3 | 24.6 | 24.4 | 24.4 | 24.6 | 25.3 | 25 | 25 | 21.4 | 21.1 | 22.3 | 23.4 | 24.8 | 26 | 17.1 | 17.2 | 23.1 | 26.7 | 28 | 27.7 | 28.4 | 27.6 |
| Mean | 24.2 | 21.9 | 21.7 | 23.7 | 25.5 | 26.1 | 25.8 | 25.9 | 25.8 | 26.2 | 27 | 23.5 | 23.9 | 25.2 | 25.9 | 26.4 | 26 | 24.1 | 23.8 | 25.4 | 26 | 28 | 27.5 | 27.3 | 26.1 |
| se | 0.5 | 0.4 | 0.2 | 0.4 | 0.5 | 0.6 | 0.5 | 0.5 | 0.6 | 0.5 | 0.6 | 0.8 | 0.8 | 0.6 | 0.8 | 0.6 | 0.8 | 1.2 | 1.2 | 1.2 | 0.9 | 0.7 | 0.5 | 0.3 | 0.6 |
| BWL % | 0.0 | −3.4 | 4.2 | 1.3 | 5.9 | 2.5 | 8.0 | 5.9 | 7.6 | 8.0 | 12.2 | 8.4 | 8.0 | 6.3 | 9.7 | 13.9 | 8.8 | 7.6 | 5.0 | 2.9 | 0.0 | 2.9 | 0.4 | −0.8 | 4.6 |

Doxo

Days from inoculum

| # | 23 | 26 | 29 | 33 | 36 | 40 | 43 | 47 | 50 | 54 | 58 | 62 | 65 | 69 | 72 | 75 |
|---|---|---|---|---|---|---|---|---|---|---|---|---|---|---|---|---|
| 25 | 25.7 | 25.6 | 26.1 | 24.6 | 25.3 | 25 | 25.6 | 26.9 | 25.9 | 25.8 | 26.1 | 26.8 | 24 | 26.6 | 26.5 | 26.9 |
| 57 | 25.2 | 24.7 | 24.8 | 24.4 | 24.2 | 25.3 | 26.3 | 27 | 26.8 | 26.6 | 26.9 | 27 | 27 | 27.9 | 27.3 | 27.8 |
| 65 | 24 | 23.8 | 25.4 | 23.5 | 24.8 | 25.3 | 26.4 | 27 | 27 | 26.1 | 26 | 27.3 | 27.7 | 29.1 | 27 | 25.9 |
| 61 | 22.8 | 22.7 | 22.7 | 22.2 | 23.4 | 23.7 | 24.4 | 25.7 | 24.2 | 24.9 | 25 | 26.2 | 25.6 | 27.4 | 26.7 | 27.1 |
| 12 | 23 | 22.7 | 23.1 | 22 | 22.8 | 24.4 | 24.9 | 26.2 | 25.3 | 25 | 25.2 | 26.2 | 26.2 | 26.8 | 27.4 | 27 |
| 21 | 23.6 | 23.1 | 22.7 | 21.4 | 21 | 21.9 | 23.7 | 25.3 | 24.4 | 23.7 | 25.8 | 24.1 | 24.5 | 25.1 | 25.1 | 25 |
| 62 | 24.5 | 22.7 | 24.1 | 23 | 24 | 24.3 | 24.6 | 25.7 | 23.9 | 25.9 | 25.7 | 26.1 | 26.2 | 27.6 | 26.5 | 27 |
| 8 | 23.6 | 23.1 | 23.1 | 22.3 | 23.8 | 24.4 | 24.6 | 25.4 | 25.2 | 25.4 | 25.3 | 26.1 | 26.1 | 27 | 26.8 | 26.1 |
| 64 | 20.6 | 19.4 | 20.4 | 18.5 | 20 | 20.1 | 21 | 21.7 | 21.2 | 21.3 | 21.3 | 22.2 | 21.5 | 22.2 | 21.1 | 22.2 |
| Mean | 23.7 | 23.0 | 23.6 | 22.4 | 23.3 | 23.8 | 24.6 | 25.7 | 24.9 | 25.0 | 25.0 | 25.8 | 25.4 | 26.6 | 26.0 | 26.1 |
| se | 0.5 | 0.6 | 0.6 | 0.6 | 0.6 | 0.6 | 0.5 | 0.5 | 0.6 | 0.5 | 0.5 | 0.5 | 0.6 | 0.6 | 0.7 | 0.6 |
| BWL % | 0.0 | −2.6 | −0.3 | −5.2 | −1.7 | 0.7 | 4.0 | 8.4 | 5.1 | 5.5 | 5.8 | 8.9 | 7.4 | 12.5 | 10.0 | 10.3 |

† sacrificed moribund

Comparing Example 1 and Example 2, EDO-S101 appears to be better tolerated in DD013 xenograft models, compared with TC-71 xenograft models. EDO-S101 was shown to be very effective against liposarcoma. The dose of 60 mg/kg administered q7dx3 resulted to be the best choice both in terms of efficacy and tolerability.

Example 3

A Phase 1/2 Study to Investigate the Safety, Pharmacokinetics and Efficacy of EDO-S101, a First-in-Class Alkylating Histone Deacetylase Inhibition (HDACi) Fusion Molecule, in Patients with Advanced Solid Tumours Purpose Phase 1: To determine the safety, tolerability, maximum tolerated dose (MTD), and recommended phase 2 dose (RP2D) of EDO-S101 as a single agent in patients with solid tumours who have progressed after at least one (1) line of standard therapy.

Phase 2: To evaluate the efficacy of EDO-S101 in selected tumour types.

| Condition | Intervention | Phase |
|---|---|---|
| Phase 1:<br>Advanced or metastatic Solid Tumours<br>Phase 2:<br>small cell lung cancer (SCLC)<br>soft tissue sarcoma or non-Kit GIST<br>triple negative breast cancer<br>ovarian cancer | Drug: EDO-S101 | Phase 1/2 |

Study Type: Interventional
Study Design: Intervention Model: Single Group Assignment
Masking: Open Label
Primary Purpose: Treatment Primary Outcome Measures Phase 1: Dose Escalation until maximum administered dose (MAD):
  Determine Maximum Tolerated Dose at optimal infusion schedule
Phase 2: Evaluation of Toxicity and Response Rate in Selected Solid Tumour Cohorts:
  Confirm recommended Phase 2 dose and optimal infusion schedule in select solid tumours
  Determine objective response rate and clinical benefit rate in selected solid tumours Secondary Outcome Measures Phase 1: Dose Escalation until MAD:
Determine maximum plasma concentration (Cmax) of EDO-S101
Phase 2: Evaluation of Toxicity and Response Rate in Selected Solid Tumour Cohorts:
  To evaluate safety and tolerability of the RP2D of the selected schedule of EDOS101.
  To determine the progression free survival time for patients who received the RP2D at the optimal infusion schedule
  To determine overall survival for patients who received the RP2D at the selected study drug administration schedule.
  To establish the trough PK profiles of EDO-S101.
  Estimated Enrollment: 158
  Phase 1:
    Schedule A: EDO-S101, IV, 60 mg/m$^2$ up to 150 mg/m$^2$ Day 1 and 15 of each 28 day cycle
    Schedule B: EDO-S101, IV, 60 mg/m$^2$ up to 150 mg/m$^2$ Day 1, 8 and 15 of each 28 day cycle
  Phase 2:
    The RP2D and selected schedule will be further investigated in patients with specific types of solid tumours: relapsed/refractory SCLC, soft tissue sarcoma, non-Kit GIST, triple negative breast, and ovarian cancers.

Detailed Description

EDO-S101 I entity, a first-in-class fusion molecule of an alkylator, bendamustine and a histone-deacetylase inhibitor (HDACi), vorinostat. This phase 1/2 study will enroll patients with solid tumours. This phase 1/2 study will enroll patients with various advanced solid tumours.

The study consists of 2 phases:
  Phase 1: Dose Escalation until MAD
  Phase 2: Evaluation of Toxicity and Response Rate in Selected Solid Tumour Cohorts The study is designed as an open label, Phase 1/2 trial of single agent EDOS101. The phase 1 portion of the study is designed to define the MTD for two (2) administration schedules by evaluating toxicities during dose escalation until MAD. The phase 2 portion of the study is designed to evaluate ORR and CBR at four (4) or six (6) months depending on the type of solid tumour.

Eligibility

Ages Eligible for Study: 18 Years and older (Adult, Senior)
Sexes Eligible for Study: All
Accepts Healthy Volunteers: No Criteria Inclusion Criteria for Phase 1 and phase 2 portions of study:
1. Signed informed consent.
2. patients ≥18 years at signing the informed consent.
3. Diagnosis of advanced or metastatic solid tumours, disease should have progressed following at least one line of standard therapy.
4. Patients with secondary metastasis to the CNS are eligible if they have met certain criteria.
5. Evaluable disease; either measurable on imaging or with informative tumour marker.
6. Discontinuation of previous cancer therapies at least three (3) weeks or 5 half-lives, whichever is shorter.
7. Eastern Cooperative Oncology Group (ECOG) performance status≤2
8. Neutrophils≥1,500 µL.
9. Platelets≥100,000 µL.
10. Aspartate aminotransferase/alanine aminotransferase (AST/ALT)≤3 upper limit of normal (ULN). In cases with liver involvement ALT/AST≤5×ULN.
11. Total bilirubin ≤1.5 mg/dL unless elevated due to known Gilbert's syndrome.
12. Creatinine≤1.5 ULN.
13. Serum potassium within normal range.
14. If female of child-bearing potential (i.e. not postmenopausal or surgically sterile), must be willing to abstain from sexual intercourse or employ an effective barrier or medical method of contraception during the study drug administration and follow-up periods. If male, must be sterile or willing to abstain from sexual intercourse or employ a barrier method of contraception during the study treatment and at least 6 months following last treatment.

Exclusion Criteria for Phase 1 and Phase 2 Portions of Study

1. Patients with primary central nervous system (CNS) cancer.
2. Patients with QTc interval >450 msec for male and >470 msec for female.
3. Patients who are on treatment with drugs known to prolong the QT/QTc interval.
4. Patients who are on treatment with Valproic Acid in any of its indication (epilepsy, mood disorder) must be excluded or must stop using the medication.
5. Any serious medical condition that interferes with adherence to study procedures.
6. Prior history of solid tumour malignancy diagnosed within the last three (3) years of study enrollment excluding adequately treated basal cell carcinoma of the skin, squamous cell carcinoma of the skin, or in situ cervical cancer, in situ breast cancer, in situ prostate cancer (patients must have shown no evidence of active disease for 2 years prior to enrollment)
7. Pregnant or breast feeding females.
8. New York Heart Association (NYHA) stage III/IV congestive heart failure, arrhythmias not adequately controlled, or other significant co-morbidities [e.g. active infection requiring systemic therapy, history of human immunodeficiency virus (HIV) infection, or active Hepatitis B or Hepatitis C].
9. Use of other investigational agents within 30 days or 5 half-lives prior to the first dose of study drug. As long as patient has recovered from any related toxicities ≥Grade 1.
10. Steroid treatment within seven (7) days prior to study treatment. Patients that require intermittent use of bronchodilators, topical steroids or local steroid injections will not be excluded from the study. Patients who have been stabilized to 10 mg orally prednisolone PO QD (or equivalent), daily or less seven (7) days prior to study drug administration are allowed.

Phase 2 Tumour-Specific Eligibility Criteria

Phase 2 patients must meet the cohort-specific inclusion/exclusion criteria in addition to the general inclusion/exclusion criteria for Phase 1 and Phase 2 study listed above.

Cohort 1 Patient Population: Relapsed/Refractory SCLC

1. Histologically or cytological confirmed limited or extensive disease stage of SCLC. The disease should be progressing during or relapsing after the previous treatment.
2. At least one line of prior combination chemotherapy including adequate doses of platinum compound and having progressed during therapy or after the previous treatment.
3. At least 3 weeks or 5 half-lives, whichever is shorter, should have elapsed since prior treatment as long as the patient recovered from any related toxicities to ≤Grade 1.
4. Prior radiotherapy is acceptable provided the patient has recovered from any radiotherapy related acute toxicities.

Cohort 2 Patient Population: Relapsed/Refractory Soft Tissue Sarcoma or Non-Kit GIST 1. Histologically confirmed diagnosis of advanced, unresectable, or metastatic soft tissue sarcoma not amenable to curative treatment with surgery or radiotherapy excluding: chondrosarcoma, neuroblastoma, osteosarcoma, embryonal rhabdomyosarcoma, or Kaposi sarcoma.
2. Must have received at least one prior first line combination chemotherapy regimen or at least two first line single-agent regimens. Adjuvant chemotherapy not considered first line, unless disease progression within 6 months of treatment.
3. The disease should be progressing/relapsed during or after the previous treatment. At least 3 weeks should have elapsed since prior chemotherapy or 5 half-lives, whichever is shorter, as long as the patient recovered from any related toxicities to ≤Grade 1.
4. Presence of measurable disease as defined by the Response Evaluation Criteria in Solid Tumours (RECIST 1.1, Eisenhauer et al. 2009).

Cohort 3 Patient Population: Relapsed/Refractory Triple Negative Breast Cancer

1. Histologically or cytologically confirmed locally advanced or metastatic Triple Negative Metastatic Breast Cancer.
2. Must have received at least one line of chemotherapy, at least 3 weeks should have relapsed since prior chemotherapy or 5 half-lives, whichever is shorter, as long as the patient recovered from acute toxicity of previous therapies to grade 1.
3. Prior radiotherapy is acceptable provided it was applied within 4 four weeks before starting of this trial and the patient recovered from any radiotherapy related acute toxicities.
4. The disease should be progressing/relapsed during or after the previous treatment.
5. Presence of measurable disease as defined by the Response Evaluation Criteria.

Cohort 4 Patient Population: Relapsed/Refractory Ovarian Cancer

1. Histologically or cytologically confirmed advanced ovarian cancer: epithelial ovarian cancer, primary peritoneal cancer or fallopian tube cancer (excluding borderline ovarian cancer) that is resistant or refractory to platinum therapy.
   a. Platinum-resistant ovarian cancer is defined as disease that responded to primary platinum therapy and then progressed within 6 months or disease that progressed during or within six months of completing a subsequent platinum therapy.
   b. Primary platinum refractory disease is defined as disease that has not responded to a platinum-based regimen or experienced disease recurrence within 3 months of completing a first-line platinum-based regimen.
2. The disease should be progressing/relapsed during or after the previous treatment. At least 3 weeks should have elapsed since prior chemotherapy or 5 half-lives, whichever is shorter, as long as the patient recovered from acute toxicity of previous therapies to ≤grade 1.
3. Presence of measurable disease as defined by the Response Evaluation Criteria in Solid tumours (RECIST 1.1, Eisenhauer et al. 2009).

The invention claimed is:

1. A method of treating sarcoma in a patient in need thereof, comprising administering to said patient an effective amount of tinostamustine or a pharmaceutically acceptable salt thereof, wherein the sarcoma is a soft tissue sarcoma, a bone sarcoma or a non-KIT gastrointestinal stromal tumour (GIST).

2. The method according to claim 1, wherein the sarcoma is from the Ewing family of tumours.

3. The method according to claim 2, wherein the sarcoma is Ewing tumour of bone.

4. The method according to claim 2, wherein the sarcoma is extraosseous Ewing tumour.

5. The method according to claim 2, wherein the sarcoma is primitive neuroectodermal tumour (PNET).

6. The method according to claim 1, wherein the sarcoma is liposarcoma.

7. The method according to claim 6, wherein the liposarcoma is well-differentiated liposarcoma, myxoid liposarcoma, pleomorphic liposarcoma, or dedifferentiated liposarcoma.

8. The method according to claim 6, wherein the lipo sarcoma is dedifferentiated liposarcoma.

9. The method according to claim 1, wherein the sarcoma is a relapsed soft tissue sarcoma, or a refractory soft tissue sarcoma, or a combination thereof.

10. The method according to claim 1, wherein tinostamustine or a pharmaceutically acceptable salt thereof is administered intravenously to the patient in need thereof at a dosage level of from 0.3 to 300 mg/m$^2$ body surface area of the patient.

11. The method according to claim 1, wherein tinostamustine or a pharmaceutically acceptable salt thereof is administered intravenously to the patient in need thereof on days 1, 8 and 15 of a 28 day treatment cycle.

12. The method according to claim 1, wherein tinostamustine or a pharmaceutically acceptable salt thereof is administered intravenously to the patient in need thereof over an infusion time of 60 minutes.

13. The method according to claim 1, wherein tinostamustine or a pharmaceutically acceptable salt thereof is administered intravenously to the patient in need thereof at a dosage level of from 80 mg/m$^2$ to 100 mg/m$^2$ body surface area of the patient, on days 1 and 15 of a 28 day treatment cycle, and over an infusion time of 60 minutes.

14. The method according to claim 1, wherein the patient is treated with tinostamustine or a pharmaceutically acceptable salt thereof and radiotherapy.

15. The method according to claim 14, wherein said radiotherapy treatment is given to the patient in need thereof at a dose of 1 to 5 Gy over 5-10 consecutive days.

16. A kit comprising tinostamustine or a pharmaceutically acceptable salt thereof together with instructions for treating sarcoma selected from soft tissue sarcoma, bone sarcoma or non-KIT gastrointestinal stromal tumour (GIST).

17. The method according to claim 10, wherein tinostamustine or a pharmaceutically acceptable salt thereof is administered at a dosage level of from 60 to 150 mg/m$^2$ body surface area of the patient.

18. The method according to claim 17, wherein tinostamustine or a pharmaceutically acceptable salt thereof is administered at a dosage level of from 80 to 100 mg/m$^2$ body surface area of the patient.

19. The method according to claim 1, wherein tinostamustine or a pharmaceutically acceptable salt thereof is administered intravenously to the patient in need thereof on days 1 and 15 of a 28 day treatment cycle.

20. The method according to claim 12, wherein tinostamustine or a pharmaceutically acceptable salt thereof is administered over an infusion time of 45 minutes.

* * * * *